US009889183B2

(12) United States Patent
Alkon

(10) Patent No.: US 9,889,183 B2
(45) Date of Patent: Feb. 13, 2018

(54) PKC ACTIVATORS AND ANTICOAGULANT IN REGIMEN FOR TREATING STROKE

(71) Applicant: BLANCHETTE ROCKEFELLER NEUROSCIENCES INSTITUTE, Morgantown, WV (US)

(72) Inventor: Daniel L. Alkon, Bethesda, MD (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 14/818,576

(22) Filed: Aug. 5, 2015

(65) Prior Publication Data
US 2016/0184414 A1 Jun. 30, 2016

Related U.S. Application Data

(62) Division of application No. 13/178,843, filed on Jul. 8, 2011, now Pat. No. 9,107,890.

(60) Provisional application No. 61/362,464, filed on Jul. 8, 2010, provisional application No. 61/412,753, filed on Nov. 11, 2010, provisional application No. 61/412,747, filed on Nov. 11, 2010.

(51) Int. Cl.
*A61K 38/49* (2006.01)
*A61K 31/20* (2006.01)
*A61K 31/366* (2006.01)
*A61K 9/00* (2006.01)

(52) U.S. Cl.
CPC ............ *A61K 38/49* (2013.01); *A61K 9/0019* (2013.01); *A61K 31/20* (2013.01); *A61K 31/366* (2013.01); *C12Y 304/21068* (2013.01)

(58) Field of Classification Search
CPC .................................................. A61K 31/20
See application file for complete search history.

(56) References Cited

FOREIGN PATENT DOCUMENTS

| JP | 2005-535660 | 11/2005 |
|---|---|---|
| JP | 2008143819 | 6/2008 |
| JP | 2010-518092 | 5/2010 |
| WO | WO 2004/004641 | 1/2004 |
| WO | WO 2004/047857 | 6/2004 |
| WO | WO 2006/031337 | 3/2006 |
| WO | WO 2008/013573 | 1/2008 |
| WO | WO 2008/100450 | 8/2008 |
| WO | WO 2010/014585 | 4/2010 |

OTHER PUBLICATIONS

Carmichael, et al., "Synchronous Neuronal Activity is a Signal for Axonal Sprouting After Cortical Lensions in the Adult," The Journal of Neuroscience, 22(14):6062-6070 (Jul. 15, 2002).
Dewar et al., "Drug development for stroke: importance of protecting cerebral white matter," European J of Pharmacology, 1999, 375:41-50.
Extended European Search Report in 14000741.0, dated Nov. 18, 2014.
Fisher et al., "Potentially effective therapies for acute ischemic stroke," Eur Neurol., 1995, 35:3-7.
Furukawa et al, "Stimulatory Effect of 4-Alkylcateochols and Their Diacetylated Derivatives on the Synthesis of Nerve Growth Factor," Biochemical Pharmacology, vol. 40, No. 10, pp. 2337-2342 (1990).
Goerge et al., "Inflammation induces hemorrhage in thrombocytopenia", Blood 111(10), Feb. 6, 2008, pp. 4958-4964.
International Search Report and Written Opinion for PCT/US2011/043346 dated Feb. 1, 2012.
International Search Report and Written Opinion for PCT/US2011/043362 dated Feb. 1, 2012.
Kennedy et al., "Differential Effects of Bryostatin 1 and Phorbol Ester on Human Breast Cancer Cell Lines", Cancer Research, 1992, 52; pp. 1278-1283.
Leys et al., "Postoke Dementia", Review, Lancet Neurol, 4:752-59 (2005).
Moroney et al., "Risk Factors for Incident Dementia After Stroke" Stroke, 24:1283-1289 (1996).
Nelson et al., "Reduction of B-Amyloid Levels by Novel Protein Kinase Ce Activators," Journal of Biological Chemistry, 284, pp. 24515-34521, 2009.
Office Action (Final) dated May 22, 2015, in U.S. Appl. No. 13/178,835.
Office Action dated May 14, 2014 in U.S. Appl. No. 13/178,843.
Office Action dated Jun. 10, 2013, U.S. Appl. No. 13/178,835.
Office Action dated Dec. 11, 2014, in U.S. Appl. No. 13/178,821.
Office Action dated Feb. 3, 2015, U.S. Appl. No. 13/553,565.
Office Action dated Mar. 27, 2013, in U.S. Appl. No. 13/178,821.
Office Action dated May 20, 2014, U.S. Appl. No. 13/553,565.
Office Action dated Nov. 1, 2013, U.S. Appl. No. 13/178,821.
Office Action dated Sep. 6, 2013, in U.S. Appl. No. 13/553,565.
Partial European Search Report EP 14000741 dated Jul. 18, 2014.
Smeda, J.S. et al, "Cerebrovascular Alterations in Protein Kinase C Mediated Constriction in Stroke-Prone Rats Editorial Comment", Stroke, vol. 30., No. 3, (Mar. 1, 1999).
Sumii et al., "Involvement of Matrix Metalloproteinase in Thrombolysis-Associated Hemorrhagic Transformation After Embolic Focal Ischemia in Rats," Stork, pp. 831-836, 2002.
Sun et al., "Poststroke neuronal rescue and synaptogenesis mediated in vivo by protein kinase C in adult brains", Proc. Natl. Acad. Sci. USA, Sep. 9, 2008; vol. 105, No. 36, pp. 13620-13625.
Sun et al., "Postischemic PKC activation rescues retrograde and anterograde long-term memory", PNAS, Aug. 26, 2009, vol. 106, No. 34, pp. 14676-14680.
Takeshi et al., "The linoleic acid derivative DPC-LA selectively activates PKC, possibly to the phosphatidylserine," Journal of Lipid Research, vol. 47, Mar. 6, 2006 pp. 1146-1156.
Tan Z. et al. "Bryostatin improves survival and reduces ischemic brain injury in aged rats after acute ischemic stroke", Stroke, vol. 44, No. 12, (Dec. 1, 2013).

(Continued)

*Primary Examiner* — Bin Shen
(74) *Attorney, Agent, or Firm* — Finnegan, Henderson, Farabow, Garrett & Dunner LLP

(57) ABSTRACT

The present disclosure provides a method for treating stroke by administering to a subject an anticoagulant, e.g., recombinant tissue plasminogen activator (rTPA), and a protein kinase C (PKC) activator followed by administration of at least one PKC activator for a duration of treatment. The methods disclosed herein may limit the size of infarction and/or reduce mortality, the disruption of the blood-brain barrier, and/or the hemorrhagic damage due to ischemic stroke compared with rTPA administration alone; and may also extend the therapeutic time window for administering rTPA after a stroke. Also disclosed are kits comprising rTPA and a PKC activator for treating stroke.

27 Claims, 18 Drawing Sheets

(56) References Cited

OTHER PUBLICATIONS

Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tham et al., "Progression of cognitive impairment after stroke; One year results from a longitudinal study pf Singaporean stroke patients," Journal of Neurological Sciences, 203-204, pp. 49-52. (2002).
The Internet Stroke Center, 1998-1999, http://www.strokecenter.org/professionals/brain-anatomy/cerebral-embolism-formation/hemorrhagic-conversion/.
Wang et al., "Treating Acute Stroke Patients With Intravenous IPA—The OSF Stroke Network Experience," Stroke 31, pp. 77-81, 2000.
Xuan et al., "Differntial Changes of Potassium Currents in CA1 Pyramidal Neurons After Transient Forebrain Ischemia," Journal of Neurophysiol, 84:2834-2843 (2000).
Office Action (Final) dated Sep. 27, 2016, in U.S. Appl. No. 13/178,835.
Adams et al., Guidelines for the Early Management of Patients With Ischemic Stroke, Stroke, vol. 34, pp. 1056-1083, 2003.
Office Action (Non-Final) dated Jun. 16, 2017, in U.S. Appl. No. 13/178,835.
Office Action dated Apr. 12, 2017, U.S. Appl. No. 13/178,821.
Parsons, et al., "Acute ischemic stroke: imaging-guided tenecteplase treatment in an extended time window." Neurology. Mar. 10, 2009;72(10):915-21.
Phillis, J.W., et al., "Mechanisms of glutamate and aspartate release in the ischemic rat cerebral cortex," Brain Research, 1996, vol. 730, 1996, pp. 150-164.
Sano, Keiji, "Acute ischaemic and delayed ischaemic neurological deficits as the causes of bad grading in aneurysmal subarachnoid haemorrhage," Neurological Research, 1994, vol. 16 , pp. 35-39.
Shimohata, T., et al., "Suppression of δPKC activation after focal cerebral ischemia contributes to the protective effect of hypothermia," J. Cerebral Blood Flow & Metabolism, 2007, 27, pp. 1463-1475.
Thomalla et al., Outcome and Symptomatic Bleeding Complications of Intravenous Thrombolysis Within 6 Hours in MRI-Selected Stroke Patients, Stroke, vol. 37, pp. 852-858, 2006.
Yoshida, Mitsuzi, et al., "Mechanism of Antitumor Action of PKC Activator, Gnidimacrin," Int. J. Cancer, 1998, vol. 77, pp. 243-250.

Chronic Bryostatin-1 Treatment Restores Spatial Learning Ability in Rats after Global Cerebral Ischemia Spatial water maze performance of rats over training trials. Data are shown as means ± SEM. Bry, bryostatin-1; Isch, cerebral ischemia; MCDA, 4-methylcatechol-diacetic acid.

Chronic Bryostatin-1 Treatment Restores Spatial Memory in Rats after Global Cerebral Ischemia (2)

Target quadrant ratio during probe test. Bry, bryostatin-1; Isch, ischemia; MCDA, 4-methylcatechol-diacetic acid *: $p < 0.05$. NS: $p > 0.05$.

PKC ACTIVATORS AND ANTICOAGULANT IN REGIMEN FOR TREATING STROKE

This application is a continuation divisional of application Ser. No. 13/178,843, filed Jul. 8, 2011, and claims priority to U.S. Provisional Application Nos. 61/362,464 filed Jul. 8, 2010, 61/412,753 filed Nov. 11, 2010, and 61/412,747 filed Nov. 11, 2010, the entire disclosures of which are incorporated by reference herein.

The present disclosure relates generally to administration of an anticoagulant, e.g., recombinant tissue plasminogen activator (rTPA), and a protein kinase C (PKC) activator followed by administering at least one PKC activator for a duration of treatment to treat a subject following ischemic stroke. The methods disclosed herein may limit the size of infarction and/or reduce mortality, the disruption of the blood-brain barrier, and/or the hemorrhagic damage due to ischemic stroke compared with rTPA administration alone. The methods disclosed herein may also extend the therapeutic window in which rTPA can be administered following a stroke and still be efficacious. Compositions and kits comprising rTPA and a PKC activator are also disclosed.

Stroke

Stroke, also known as a cerebrovascular accident (CVA), is a medical emergency and can cause permanent neurologic damage or even death if not promptly diagnosed and treated. It is the third leading cause of death and the leading cause of adult disability in the United States and industrialized European nations. On average, a stroke occurs every 45 seconds and someone dies every 3 minutes. Of every 5 deaths from stroke, 2 occur in men and 3 in women.

A stroke is an acute neurological injury in which the blood supply to a part of the brain is interrupted, leading to the sudden loss of neuronal function. The blood supply to the brain may be interrupted in several ways; the disturbance in perfusion is commonly arterial, but may be venous.

Different types of stroke include ischemic stroke and hemorrhagic stroke. Ischemic stroke or cerebral ischemia is caused by a temporary or permanent restriction of cerebral blood flow and oxygen supply caused by, for example, an embolis (embolic stroke) or blood clot (thrombolyic stroke). In contrast, a hemorrhagic stroke is caused by the blood vessel rupture (e.g., ruptured aneurysm), which leads to severe bleeding in the brain.

In stroke, the part of the brain with disturbed perfusion no longer receives adequate oxygen (hypoxia). This initiates the ischemic cascade which causes brain cells to die or be seriously damaged, impairing local brain function. A transient ischemic attack (TIA) or "mini-stroke" normally lasts less than 24 hours, but is associated with the same symptoms as stroke such as sudden numbness or weakness of the face, arm, or leg; sudden confusion, trouble speaking or understanding; sudden trouble seeing in one or both eyes; and/or sudden trouble walking, dizziness, loss of balance or coordination. Typically, TIAs do not result in permanent brain injury through acute infarction (i.e., tissue death) but they may indicate serious risk of subsequent stroke. An infarctive stroke typically involves a more severe vessel blockage that can last longer than 24 hours without intervention. Cerebral infarctions vary in severity; about one third of the cases result in death.

Ischemia may be confined to a specific region of the brain (focal ischemia), or may affect large areas of brain tissue (global ischemia). Significant brain injury can occur after the immediate ischemic event. Neuronal death and injury after cerebral ischemia involve pathological changes associated with necrosis and delayed apoptosis. Neurons in the infarction core of focal, severe stroke are immediately dead and cannot be saved by pharmacologic intervention. The ischemic penumbra, consisting of the brain tissue around the core in focal ischemic stroke, and the sensitive neurons/network in global cerebral ischemia, however, are maintained by a diminished blood supply. The damage to this penumbral brain tissue occurs in a "delayed" manner, starting 4-6 hours as the second phase or days and weeks later as the so-called third phase, after ischemic stroke.

A consistent consequence of cerebral ischemia/hypoxia in humans and other mammals is central nervous system dysfunction, the nature of which depends on the location and extent of injury. Global cerebral ischemia/hypoxia selectively injures or damages the pyramidal neurons in the dorsal hippocampal CA1 area, which are essential for episodic memory, providing a sensitive measure for monitoring ischemic damage and recovery functionally. After a cerebral ischemia of about 15 minutes, for example, the hippocampal CA1 pyramidal cells start to degenerate within 2-3 days, and reach the maximal extent of cell death a week after the ischemic event. The sensitive neuronal structures in global cerebral ischemia and the ischemic penumbra are "at-risk" tissues. Their salvage through intervention or further damage in the subsequent days or weeks determine dramatic differences in long-term disability.

Following ischemic stroke, there is a transient loss of blood-brain barrier (BBB) function that happens within minutes or hours of the event as the interruption in blood flow and lack of oxygen leads to increased BBB permeability. DiNapoli et al., *Neurobiology of Aging* (2008) vol. 29, pp. 753-764. Disruption of the BBB, in turn, results in loss of ionic homeostasis and loss of neurotransmitter homeostasis. Immune cells and toxic compounds can enter the brain during that period, providing an added neurotoxic insult. Edema can form during the early stages of ischemia with a rate related to the rate of sodium transport from blood to brain, i.e., increased sodium transport across the BBB contributes to cerebral edema formation. Betz and Coester, *Stroke* (1990), vol. 21, pp. 1199-1204. Thus, measurements of both edema and ion uptake in the brain are indicators of brain pathology following stroke. The loss of integrity of the barrier could lead to adverse hemorrhages as a consequence of thrombolytic therapy, e.g., administration of recombinant tissue plasminogen activator (rTPA). Tanne et al., *Nature Reviews Neurology* (2008), vol. 4, pp. 644-645.

Despite the medical emergency presented by stroke, and preclinical studies suggesting agents that may be effective in arresting the pathological processes involved, options for treating stroke remain limited. The main treatment available is rTPA, a thrombolytic agent and the only drug currently approved by the U.S. Food and Drug Administration for acute/urgent treatment of ischemic stroke. The rTPA protein is an enzyme (serine protease) that initiates local fibrinolysis via fibrin-enhanced conversion of plasminogen to plasmin. rTPA is used to improve neurologic recovery and reduce the incidence of disability. Experimental models of stroke use rTPA, for example, in reperfusion after inducing focal embolic ischemia via middle cerebral artery occlusion (MCAO). DiNapoli et al., *J. Neurosci Methods* (2006), vol. 154, pp. 233-238.

The effectiveness of rTPA and other potential agents for arresting infarct development depends on early administration or even before the ischemic event, if possible. Treatment with rTPA is designed to achieve early arterial recanalization such that rTPA must be administered within 3 hours after the event to be effective. This time dependency limits its clinical usefulness; the narrow therapeutic time window and exclusion criteria in treating ischemic stroke leads to about only 5% of candidate patients receiving effective intravenous thrombolytic therapy. For example, one study reported 13% mortality at 30 days after an acute ischemic stroke, with more than two thirds of the deaths related to the initial stroke. Nedeltcheva et al., *Swiss Med. Wkly* (2010), vol. 140, pp. 254-259. The recommended dose of rTPA is 0.9 mg/kg (maximum dose 90 mg) where 10% is given by rapid (~1 min.) Iv injection and the remainder by constant infusion over 60 min. No aspirin, heparin, or warfarin should be administered for 24 hours following rTPA. rTPA is sold under the names alteplase (Activase®) and streptokinase (Streptase®).

Use of rTPA following stroke is controversial because it carries an increased risk of intracranial hemorrhage, reperfusion injury, and diminishing cerebral artery reactivity. Thus, rTPA is should not be administered to treat hemorrhagic stroke. Unfortunately, it may not be immediately apparent whether a patient suffered an ischemic or hemorrhagic stroke, which further limits the usefulness of rTPA within its limited therapeutic time window. In addition, hemorrhagic transformation can spontaneously follow ischemic stroke. For example, one study found that 6.4% of patients with large strokes developed substantial brain hemorrhage as a complication from being given rTPA. The National Institute of Neurological Disorders and Stroke rt-PA Stroke Study Group, *N. Engl. J. Med.* (1995), vol. 333, pp. 1581-1587.

rTPA is contraindicated or advised against in the following patient populations:
 Evidence of intracranial hemorrhage on pretreatment CT scan
 Clinical presentation suggestive of subarachnoid hemorrhage, even with normal CT scan
 Active internal bleeding
 Known bleeding diathesis, including but not limited to: having a platelet count <100,000/mm; receiving heparin within 48 hours and having an elevated activated partial thromboplastin (aPTT) greater than upper limit of normal for laboratory; and current use of oral anticoagulants (e.g., warfarin sodium) or recent use with an elevated prothrombin time >15 seconds
 Within 3 months any intracranial surgery, serious head trauma, or previous stroke
 History of gastrointestinal or urinary tract hemorrhage within 21 days
 Recent arterial puncture at a noncompressible site
 Recent lumbar puncture
 On repeated measurements, systolic blood pressure greater than 185 mm Hg or diastolic blood pressure greater than 110 mm Hg at the time treatment is to begin, and patients requiring aggressive treatment to reduce blood pressure to within these limits.
 History of intracranial hemorrhage
 Abnormal blood glucose (<50 mg/dL or >400 mg/dL)
 Post myocardial infarction pericarditis
 Patient observed to have seizure at the same time the onset of stroke symptoms were observed
 Known arteriovenous malformation, or aneurysm See, e.g., TPA Stroke Study Group Guidelines, The Brian Attack Coalition (available at www.stroke-site.org/guidelines/tpa_guidelines.html).

Studies have suggested an association between hematocrit, reduced reperfusion and greater infarct size, and between elevated hemoglobin levels and increased rates of all-cause death. Tanne et al., *BMC Neurology* (2010), vol. 10:22, pp. 1-7. Elevated levels of glycated hemoglobin (HbA1c) increases the risk of heart attacks and strokes in diabetic patients. Glycated hemoglobin, even at levels considered in the normal range, can also be an independent predictor of ischemic stroke in non-diabetic adults. Selvin et al., *N. Engl. J. Med.* (2010), vol. 362, pp. 800-811. Elevated hemoglobin may also increase the risk of stroke in patients with chronic kidney disease.

Low hemoglobin levels (e.g., levels>6.0% or 8.8 g/dL, anemia) have also been identified as a risk factor for ischemic stroke, especially following cardiac surgery. In addition, anemia can worsen brain ischemia following acute ischemic stroke, and is associated with a poor prognosis and increased mortality after one year compared with non-anemic stroke patients (hemoglobin<13 g/dL in males, <12 g/dL in women). Tanne et al., *BMC Neurology* (2010), 10:22. Studies have also reported that children with sickle cell anemia have an increased stroke risk.

Protein Kinase C

Protein kinase C (PKC) is one of the largest gene families of non-receptor serine-threonine protein kinases. Since the discovery of PKC in the early eighties and its identification as a major receptor for phorbol esters, a multitude of physiological signaling mechanisms have been ascribed to this enzyme. Kikkawa et al., *J. Biol. Chem.* (1982), vol. 257, pp. 13341-13348; Ashendel et al., *Cancer Res.* (1983), vol. 43: 4333-4337. The interest in PKC stems from its unique ability to be activated in vitro by calcium and diacylglycerol (and phorbol ester mimetics), an effector whose formation is coupled to phospholipid turnover by the action of growth and differentiation factors. Activation of PKC involves binding of 1,2-diacylglycerol (DAG) and/or 1,2-diacyl-sn-glycero-3-phospho-L-serine (phosphatidyl-L-serine, PS) at different binding sites. An alternative approach to activating PKC directly is through indirect PKC activation, e.g., by activating phospholipases such as phospholipase Cγ, by stimulating the Ser/Thr kinase Akt by way of phosphatidylinositol 3-kinase (PI3K), or by increasing the levels of DAG, the endogenous activator. Nelson et al., *Trends in Biochem. Sci.* (2009) vol. 34, pp. 136-145. Diacylglycerol kinase inhibitors, for example, may enhance the levels of the endogenous ligand diacylglycerol, thereby producing activation of PKC. Meinhardt et al., *Anti-Cancer Drugs* (2002), vol. 13, pp. 725-733. Phorbol esters are not suitable compounds for eventual drug development because of their tumor promotion activity. Ibarreta et al. *Neuroreport* (1999), vol. 10, pp. 1035-1040).

The PKC gene family consists of 11 genes, which are divided into four subgroups: (1) classical PKC α, β1, β2 (β1 and β2 are alternatively spliced forms of the same gene) and γ; (2) novel PKC δ, ε, η, and θ; (3) atypical PKC ζ and ι/λ; and (4) PKC μ. PKC μ resembles the novel PKC isoforms but differs by having a putative transmembrane domain. Blobe et al. *Cancer Metastasis Rev.* (1994), vol. 13, pp. 411-431; Hug et al. *Biochem. J.* (1993) vol. 291, pp. 329-343; Kikkawa et al. *Ann. Rev. Biochem.* (1989), vol. 58, pp. 31-44. The classical PKC isoforms α, β1, β2, and γ are $Ca^{2+}$, phospholipid, and diacylglycerol-dependent whereas the other isoforms are activated by phospholipid, diacylglycerol but are not dependent on $Ca^{2+}$ and no activator may be necessary. All isoforms encompass 5 variable (VI-V5) regions, and the α, β, and γ isoforms contain four (C1-C4) structural domains which are highly conserved. All isoforms except PKC α, β, and γ lack the C2 domain, the ι/λ and η isoforms also lack nine of two cysteine-rich zinc finger domains in C1 to which diacylglycerol binds. The C1 domain also contains the pseudosubstrate sequence which is highly conserved among all isoforms, and which serves an autoregulatory function by blocking the substrate-binding site to produce an inactive conformation of the enzyme. House et al., *Science* (1987), vol. 238, pp. 1726-1728.

Because of these structural features, diverse PKC isoforms are thought to have highly specialized roles in signal transduction in response to physiological stimuli as well as in neoplastic transformation and differentiation. Nishizuka, *Cancer*(1989), vol. 10, pp. 1892-1903; Glazer, pp. 171-198 in *Protein Kinase C*, I. F. Kuo, ed., Oxford U. Press, 1994. For a discussion of PKC modulators see, for example, International Application No. PCT/US97/08141 (WO 97/43268) and U.S. Pat. Nos. 5,652,232; 6,080,784; 5,891,906; 5,962,498; 5,955,501; 5,891,870 and 5,962,504, each incorporated by reference herein in its entirety.

Fatty Acids as PKC Activators

Some polyunsaturated fatty acids (PUFAs) such as arachidonic acid (5,8,11,14-eicosatetraenoic acid) are known natural activators of PKC. Docosahexaenoic acid (DHA) (all-cis-docosa-4,7,10,13,16,19-hexaenoic acid), for example, is a PKC activator and has been shown to slow the accumulation of Aβ and tau proteins associated with brain-clogging plaques and tangles implicated in Alzheimer's disease. Sahlin et al., *Eur. J. Neurosci.* (2007), vol. 26, pp. 882-889. Some PUFA derivatives also have reported PKC activity. Kanno et al., *J. Lipid Res.* (2007), vol. 47, pp. 1146-1156.

Problems associated with use of PUFAs as PKC activators include a need for high concentrations to achieve effects, non-specific activation of PKC isoforms, and rapid metabolism and sequestration of unmodified PUFAs into fat tissues and other organs where they are incorporated into triglycerides and chylomicrons. Ishiguro et al., *J. Pharmacobiodyn* (1988) vol. 11, pp. 251-261. PUFAs may also cause adverse side effects. For example, arachidonic acid is a biochemical precursor to prostaglandins, thromboxanes, and leukotrienes, which have potent pro-inflammatory effects. This may be undesirable for treatment of some diseases like Alzheimer's disease, whose pathology likely involves inflammation. Other essential fatty acids may also cause biological effects such as enhancing nitric oxide signaling, anti-inflammatory effects, and inhibition of HMG-CoA reductase, which could interfere with cholesterol biosynthesis.

The activation of PKC has been shown to improve learning and memory. See, e.g., Hongpaisan et al., *Proc. Natl. Acad. Sci.* (2007) vol. 104, pp. 19571-19578; International Application Nos. PCT/US2003/007101 (WO 2003/075850); PCT/US2003/020820 (WO 2004/004641); PCT/US2005/028522 (WO 2006/031337); PCT/US2006/029110 (WO 2007/016202); PCT/US2007/002454 (WO 2008/013573); PCT/US2008/001755 (WO 2008/100449); PCT/US2008/006158 (WO 2008/143880); PCT/US2009/051927 (WO 2010/014585); and PCT/US2011/000315; and U.S. application Ser. Nos. 12/068,732; 10/167,491 (now U.S. Pat. No. 6,825,229); Ser. Nos. 12/851,222; 11/802,723; 12/068,742; and 12/510,681; each incorporated by reference herein in its entirety. PKC activators have been used to treat memory and learning deficits induced by stroke upon administration 24 hours or more after inducing global cerebral ischemia through two-vessel occlusion combined with a short term (~14 minutes) systemic hypoxia. Sun et al., *Proc. Natl. Acad. Sci.* (2008) vol. 105, pp. 13620-13625; Sun et al., *Proc. Natl. Acad. Sci.* (2009) vol. 106, pp. 14676-14680.

The present disclosure relates to a method of treating a subject who has suffered an ischemic event comprising: (a) administering to the subject an anticoagulant and at least one protein kinase C (PKC) activator within about 24 hours after the ischemic event; and (b) administering at least one PKC activator after step (a) for a duration of treatment; wherein the PKC activators of step (a) and step (b) are the same or different.

The present disclosure further relates to a method of treating stroke in a subject in need thereof comprising: (a) identifying a subject having suffered a stroke; (b) administering to the subject a therapeutically-effective amount of a protein kinase C (PKC) activator; (c) determining whether the subject suffered an ischemic stroke or hemorrhagic stroke; (d) if the subject suffered an ischemic stroke, administering a therapeutically-effective amount of an anticoagulant; and (e) administering at least one PKC activator for a duration of treatment; wherein the PKC activators of step (b) and step (e) are the same or different.

BRIEF DESCRIPTION OF THE DRAWINGS

(FIG. 13b) various concentrations of bryostatin on TACE activity in rat cortical primary neurons; and (FIG. 13c) BR-111 (DHA-CP6) on TACE activity in rat cortical primary neurons.

DETAILED DESCRIPTION

Figure 1:
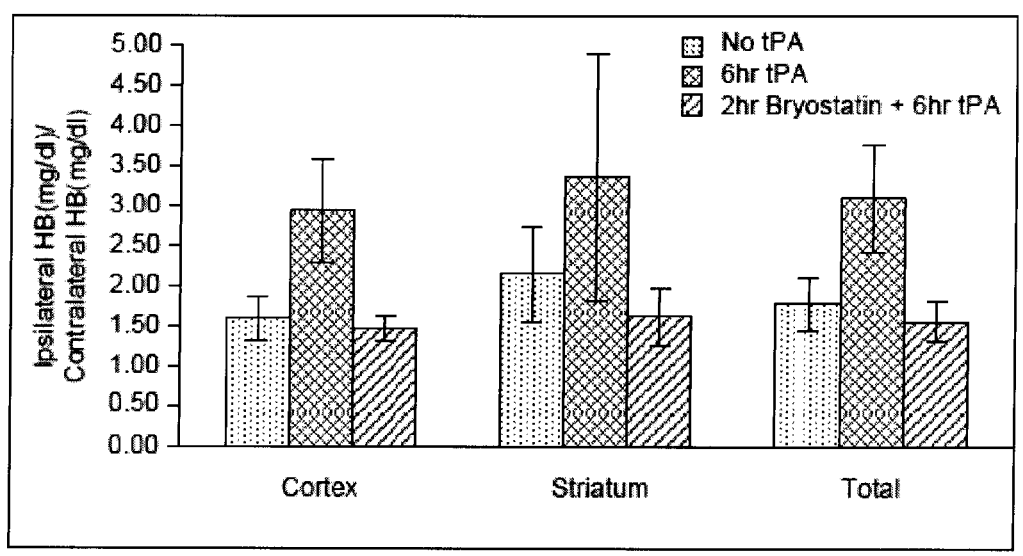
FIG. 1 shows a the amount of hemoglobin the ipsilateral and contralateral cortices following ischemic stroke in rats treated with either rTPA at 6 hours following stroke, or a combination of bryostatin-1 administered 2 hours after the stroke, followed 6 hours later by rTPA.

Particular aspects of the disclosure are described in greater detail below. The terms and definitions as used in the present application and as clarified herein are intended to represent the meaning within the present disclosure. The patent and scientific literature referred to herein is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value including an acceptable degree of error for the quantity measured given the nature or precision of the measurements. As used herein, the terms "approximately" and "about" should be generally understood to encompass ±20% of a specified amount, frequency or value. Numerical quantities given herein are approximate unless stated otherwise, meaning that term "about" or "approximately" can be inferred when not expressly stated.

The terms "administer," "administration," or "administering" as used herein refer to (1) providing, giving, dosing and/or prescribing by either a health practitioner or his authorized agent or under his direction a composition according to the disclosure, and (2) putting into, taking or consuming by the patient or person himself or herself, a composition according to the disclosure. As used herein, "administration" of a composition includes any route of administration, including oral, intravenous, subcutaneous, intraperitoneal, and intramuscular.

As used herein, the term "subject" means a mammal, i.e., a human or a non-human mammal.

The phrase "a therapeutically effective amount" refers to an amount of a therapeutic agent that results in a measurable therapeutic response. A therapeutic response may be any response that a user (e.g., a clinician) will recognize as an effective response to the therapy, including improvement of symptoms and surrogate clinical markers. Thus, a therapeutic response will generally be an amelioration or inhibition of one or more symptoms of a disease or condition, e.g., stroke. A measurable therapeutic response also includes a finding that a symptom or disease is prevented or has a delayed onset, or is otherwise attenuated by the therapeutic agent. thus, a "therapeutically effective amount" as used herein refers to an amount sufficient to reduce one or more symptom(s) or condition(s) associated with an ischemic stroke including but not limited to hemorrhagic transformation, disruption of the blood-brain barrier, increase in hemoglobin levels, and mortality.

As used herein, "protein kinase C activator" or "PKC activator" means a substance that increases the rate of the reaction catalyzed by protein kinase C by binding to the protein kinase C.

As used herein "macrocyclic lactone" refers to a compound comprising a macrolide ring, i.e., a large macrocyclic lactone ring to which one or more deoxy sugars may be attached.

Fatty acids according to the present disclosure may be saturated or unsaturated, branched or unbranched, and naturally-occurring or synthetic.

The term "monounsaturated fatty acid" (MUFA) refers to a fatty acid comprising a single C═C double bond with the remaining carbon atoms in the chain singly-bonded; MUFAs are also called "monoenoic fatty acids." Examples of MUFAs include, but are not limited to, oleic acid, myristoleic, acid and palm itoleic acid.

The term "cis-MUFA" refers to MUFAs wherein the hydrogen atoms adjacent to the C═C double bond are on the same side of the double bond.

The term "polyunsaturated fatty acid" (PUFA) refers to a fatty acid comprising more than one C═C double bond; PUFAs are also called "polyenoic fatty acids." PUFAs include, but are not limited to, omega-3 fatty acids, omega-6 fatty acids, and omega-9 fatty acids; wherein the first C═C double bond is located 3, 6, and 9 carbons, respectively, from the last carbon in the chain farthest from the carboxylic acid group (known as the "omega carbon"). The abbreviation X:Y indicates an acyl group containing X carbon atoms and Y double bonds. For example, linoleic acid would be abbreviated 18:2. Examples of PUFAs include, but are not limited to, linoleic acid (9,12-octadecadienoic acid); γ-linolenic acid (GLA; 6,9,12-octadecatrienoic acid); α-linolenic acid (9,12,15-octadecatrienoic acid); arachidonic acid (5,8,11,14-eicosatetraenoic acid); eicosapentanoic acid (EPA; 5,8,11,14,17-eicosapentanoic acid); docosapentaenoic acid (DPA; 7,10,13,16,19-docosapentaenoic acid); docosahexaenoic acid (DHA; 4,7,10,13,16,19-docosahexanoic acid); and stearidonic acid (6,9,12,15-octadecatetraenoic acid). Sources of PUFAs include marine fish and vegetable oils derived from oil seed crops. PUFAs in commercially-developed plant oils may comprise, for example, linoleic acid and/or linolenic acid.

The term "cis-PUFA" refers to a PUFA wherein the carbon atoms adjacent to a C═C double bond are on the same side of the double bond.

The term "methylene-interrupted polyene" refers to a PUFA comprising two or more cis C═C double bonds separated from each other by a single methylene (—CH$_2$—) group. The terms "non-methylene-interrupted polyene" and "polymethylene-interrupted fatty acid" refer to a PUFA having two or more cis C═C double bonds separated by more than one methylene group.

Conjugated fatty acids such as conjugated linoleic acid (9-cis,11-trans-octadecadienoic acid, an isomer of all-cis-9,12-octadecadienoic acid) have a conjugated diene, i.e., C═C double bonds on adjacent carbons. Some evidence suggests that conjugated linoleic acid may have antitumor activity.

The term "cyclopropyl group" refers to a cycloalkane group of three carbon atoms linked to form a three-membered ring (—CHCH$_2$CH—).

The term "epoxyl group" refers to a heterocyclic group comprising two carbon atoms and an oxygen atom linked to form a three-membered ring (—CHOCH—).

The term "PUFA derivative" refers to a PUFA, or alcohol or ester thereof, in which at least one of the C=C double bonds is cyclopropanated or epoxidized.

The term "MUFA derivative" refers to a MUFA, or alcohol or ester thereof, in which the C=C double bond is cyclopropanated or epoxidized.

As used herein, "selective activation" means activation of one PKC isozyme, e.g., PKCε, to a greater detectable extent than any other PKC isozyme.

The term "neurodegeneration" refers to the progressive loss of structure or function of neurons, including death of neurons.

The term "pharmaceutically acceptable" refers to molecular entities and compositions that are physiologically tolerable and do not typically produce untoward reactions when administered to a subject.

While the present disclosure generally describes use of rTPA, other anticoagulants and anticoagulant therapies suitable for the treatment of stroke are also contemplated. Further, it is understood that the present disclosure is not limited to a specific manufactured type of TPA (e.g., rTPA), but includes TPA generally.

The present disclosure generally relates to methods of treating stroke comprising an initial treatment of administering an anticoagulant, e.g., rTPA, and a PKC activator followed by a subsequent treatment of administering a PKC activator. In some embodiments, the initial administration of a PKC activator may extend the time that rTPA can be administered after a stroke (e.g., after an ischemic event) while still retaining efficacy. The subsequent administration of a PKC activator may provide additional protective, preventative, and/or regenerative benefits such as, for example, antiapoptosis, antisynaptic loss, and/or synaptogenesis. The methods disclosed herein may, for example, reduce mortality, reduce hemorrhagic transformation, reduce disruptions to the blood-brain barrier (BBB), and/or reduce the level of assayed hemoglobin, wherein elevated hemoglobin is a risk factor for reduced reperfusion, greater infarction size, and/or mortality due to stroke. Further, the methods disclosed herein may improve cognitive capacity, learning, and/or memory following stroke, and may reverse stroke-induced brain injury and/or stroke-induced memory impairment.

Sliding Temporal Window

In the methods presently disclosed, a PKC activator may be administered before, after, and/or at the same time as rTPA for the initial treatment. In some embodiments of the present disclosure, rTPA and a PKC activator are administered at the same time. Thus, the present disclosure contemplates "sliding temporal windows" for administration of a PKC activator and rTPA to a subject. The term "sliding temporal window" refers to the notion that a PKC activator and rTPA can be administered in any order to a subject that has suffered a stroke, at any time relative to one another, and at any time relative to when the stroke occurred.

At least four scenarios are contemplated:

Scenario 1:

In some embodiments of the present disclosure, a PKC activator may be administered to a subject within a given time period after suffering a stroke, followed by rTPA after another period of time. The PKC activator may be administered at any time after the occurrence of a stroke, generally within about 24 hours. For example, the PKC activator may be administered to a subject about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after a stroke. The rTPA may then be administered to the subject about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after the PKC activator.

For example, in some embodiments, the PKC activator is administered within 24 hours after the ischemic event, such as from about 1 hour to about 12 hours or from about 2 hours to about 6 hours after the ischemic event. rTPA is then administered within 24 hours after administration of the PKC activator, such as from about 1 hour to about 12 hours or from about 2 hours to about 6 hours after administration of the PKC activator. In one embodiment, the PKC activator is administered within about 6 hours after the ischemic event and the rTPA is administered within about 2 hours after administration of the PKC activator. In another embodiment, the PKC activator is administered about 3 hours after the ischemic event and the rTPA is administered about 2 hours after the PKC activator.

Scenario 2:

In some embodiments, rTPA may be administered to a subject within a given time period after suffering a stroke, followed by administration of a PKC activator after another period of time. The rTPA may be administered at any time after the occurrence of a stroke, generally within about 24 hours. For example, the rTPA may be administered to a subject about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after a stroke. The PKC activator may then be administered to the subject about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after administration of the rTPA.

For example, in some embodiments, the rTPA is administered within 24 hours after the ischemic event, such as from about 1 hour to about 12 hours or from about 2 hours to about 6 hours after the ischemic event. The PKC activator is then administered within 24 hours after administration of the rTPA, such as from about 1 hour to about 12 hours or from about 2 hours to about 6 hours after the rTPA. In one embodiment, rTPA is administered within about 6 hours after the ischemic event and the PKC activator is administered within about 2 hours after the rTPA. In another embodiment, rTPA is administered about 3 hours after the ischemic event and the PKC activator is administered about 2 hours after the rTPA.

Scenario 3:

In other embodiments of the present disclosure, a PKC activator may be administered to a subject within a given time period after suffering a stroke, followed by rTPA one or more times after another period of time, and further followed by administration of a PKC activator one or more times a period of time later. For example, the PKC activator may be administered to a subject about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after a stroke. The rTPA may then be administered to the subject about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after administration of the PKC activator. Thereafter, another PKC activator may be administered about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours after administration of the rTPA. The PKC activator administered before and after rTPA may be the same or different.

Similarly, rTPA may be administered to a subject one or more times within a given time period after having suffered a stroke, followed by a PKC activator one or more times after another time period, and further followed by administration of the same or a different PKC activator one or more times a period of time later.

Scenario 4:

In yet other embodiments, a PKC activator and rTPA may be administered at the same time to a subject after suffering a stroke. This may be done by directly administering a composition comprising a PKC activator and rTPA, or administering a composition comprising a PKC activator and a separate composition comprising rTPA in rapid succession, one after the other in either order (i.e., the composition comprising a PKC activator may be administered first or the composition comprising rTPA may be administered first).

In some embodiments, the present disclosure provides a method for extending the therapeutic window for treating ischemic stroke with rTPA comprising administering a PKC activator before, after, or at the same time as rTPA. The recommended time period for administering rTPA (e.g., Activase®) is about 3 hours. In one embodiment of the present disclosure, for example, a PKC activator is administered to a subject about 2 hours after a stroke followed by administration of rTPA about 6 hours later (i.e., about 8 hours after the stroke). In another embodiment, rTPA is administered to a subject about 6 hours after a stroke followed by administration of a PKC activator about 2 hours later (i.e., about 8 hours after the stroke).

At least one embodiment of the present disclosure provides for treatment of a subject who has suffered a stroke before it is known whether the subject suffered an ischemic stroke or a hemorrhagic stroke. For example, the present disclosure provides for a method of identifying a subject who has suffered a stroke, administering a therapeutically-effective amount of a PKC activator, and determining whether the subject suffered an ischemic stroke or a hemorrhagic stroke. The determination regarding the type of stroke suffered may be made by any suitable means known in the medical arts including, for example, a computed tomography (CT) scan. If the subject suffered an ischemic stroke, a therapeutically-effective amount of rTPA may be administered. If the subject suffered a hemorrhagic stroke, however, rTPA is not administered. Thus, in some embodiments of the present disclosure, extending the therapeutic time window for treating stroke with rTPA allows for a determination of whether a subject suffered an ischemic stroke or a hemorrhagic stroke.

In the methods disclosed herein the initial treatment of rTPA and PKC activator, for example described in scenarios 1-4, is followed by a subsequent treatment of a PKC activator. The subsequent treatment of PKC activator may be initiated, for example, from about 10 hours to about 32 hours after the ischemic event, such as about 24 hours after the ischemic event. The PKC activators administered in the initial treatment and the subsequent treatment may be the same or different. In some embodiments, the PKC activator is administered from 1-3 times per week. In some embodiments, the duration of treatment ranges from about 1 week to about 10 weeks, such as from about 1 week to about 6 weeks, for example about 1 week, about 2 weeks, about 3 weeks, about 4 weeks, about 5 weeks, or about 6 weeks.

PKC Activators

In some embodiments of the present disclosure, the PKC activator may activate PKCε at least 1-fold, 2-fold or 5-fold over other PKC isozymes, for example as measured via a PKC activation assay as described herein. Upon activation, PKC enzymes are translocated to the plasma membrane by RACK (receptor for activated C-kinase) proteins, which are membrane-bound receptors for activated PKC. In general, upon activation, PKC enzymes are translocated to the plasma membrane by RACK proteins. Other indicia of PKC activation include phosphorylation at specific C-terminal serine/threonine residues by phosphatidylinositol-trisphosphate-dependent kinase (PDK1), with at least two additional phosphorylations and/or autophosphorylations of well-conserved sequences in each enzyme of the PKC family. Activation of PKC is described, for example, in Sun et al., *Recent Patents CNS Drug Discov.* (2006), vol. 1, pp. 147-56.

PKC activators suitable for the methods, compositions, and kits disclosed herein include, for example, macrocyclic lactones, e.g., bryostatin and neristatin classes, that act to stimulate PKC. Of the bryostatin class of compounds, bryostatin-1 has been shown to activate PKC without tumor promotion. Bryostatin-1 may be particularly useful as a PKC activator because the dose response curve is biphasic and bryostatin-1 demonstrates differential regulation of PKC isozymes including PKCα, PKCδ and PKCε. Bryostatin-1 has undergone toxicity and safety studies in animals and humans, and is actively investigated as an anti-cancer agent.

Macrocyclic lactones generally comprise 14-, 15-, or 16-membered lactone rings. Macrolides belong to the polyketide class of natural products. Macrocyclic lactones and derivatives thereof are described, for example, in U.S. Pat. Nos. 6,187,568; 6,043,270; 5,393,897; 5,072,004; 5,196,447; 4,833,257; and 4,611,066; and 4,560,774; each incorporated by reference herein in its entirety. Those patents describe various compounds and various uses for macrocyclic lactones including their use as an anti-inflammatory or anti-tumor agent. Szallasi et al. *J. Biol. Chem.* (1994), vol. 269, pp. 2118-2124; Zhang et al., *Cancer Res.* (1996), vol. 56, pp. 802-808; Hennings et al. *Carcinogenesis* (1987), vol. 8, pp. 1343-1346; Varterasian et al. *Clin. Cancer Res.* (2000), vol. 6, pp. 825-828; Mutter et al. *Bioorganic & Med. Chem.* (2000), vol. 8, pp. 1841-1860; each incorporated by reference herein in its entirety. The bryostatin and neristatin compounds were originally isolated from the marine bryozoan *Bugula neritina* L.

In one embodiment, for example, the PKC activator is a macrocyclic lactone, such as a bryostatin or neristatin. Bryostatins include, for example, bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, and bryostatin-18. In at least one embodiment, the bryostatin is bryostatin-1. Neristatins suitable for the present disclosure include, for example, neristatin-1.

Analogs of bryostatin, commonly referred to as bryologs, are one particular class of PKC activators that are suitable for use in the present disclosure. Table 1 summarizes structural characteristics of several bryologs and demonstrates variability in their affinity for PKC (ranging from 0.25 nM to 10 μM). Structurally, they are all similar. While bryostatin-1 has two pyran rings and one 6-membered cyclic acetal, in most bryologs one of the pyrans of bryostatin-1 is replaced with a second 6-membered acetal ring. This modification reduces the stability of bryologs, relative to bryostatin-1, for example, in both strong acid or base, but has little significance at physiological pH. Bryologs also have a lower molecular weight (ranging from about 600 g/mol to 755 g/mol), as compared to bryostatin-1 (988), a property which facilitates transport across the blood-brain barrier.

TABLE 1

Bryologs.

| Name | PKC Affin (nM) | MW | Description |
| --- | --- | --- | --- |
| Bryostatin-1 | 1.35 | 988 | 2 pyran + 1 cyclic acetal + macrocycle |
| Analog 1 | 0.25 | 737 | 1 pyran + 2 cyclic acetal + macrocycle |
| Analog 2 | 6.50 | 723 | 1 pyran + 2 cyclic acetal + macrocycle |
| Analog 7a | — | 642 | 1 pyran + 2 cyclic acetals + macrocycle |
| Analog 7b | 297 | 711 | 1 pyran + 2 cyclic acetals + macrocycle |
| Analog 7c | 3.4 | 726 | 1 pyran + 2 cyclic acetals + macrocycle |
| Analog 7d | 10000 | 745 | 1 pyran + 2 cyclic acetals + macrocycle, acetylated |
| Analog 8 | 8.3 | 754 | 2 cyclic acetals + macrocycle |
| Analog 9 | 10000 | 599 | 2 cyclic acetals |

Analog 1 exhibits the highest affinity for PKC. Wender et al., *Curr. Drug Discov. Technol.* (2004), vol. 1, pp. 1-11; Wender et al. *Proc. Natl. Acad. Sci.* (1998), vol. 95, pp. 6624-6629; Wender et al., *J. Am. Chem. Soc.* (2002), vol. 124, pp. 13648-13649, each incorporated by reference herein in their entireties. Only Analog 1 exhibits a higher affinity for PKC than bryostatin. Analog 2, which lacks the A ring of bryostatin-1, is the simplest analog that maintains high affinity for PKC. In addition to the active bryologs, Analog 7d, which is acetylated at position 26, has virtually no affinity for PKC.

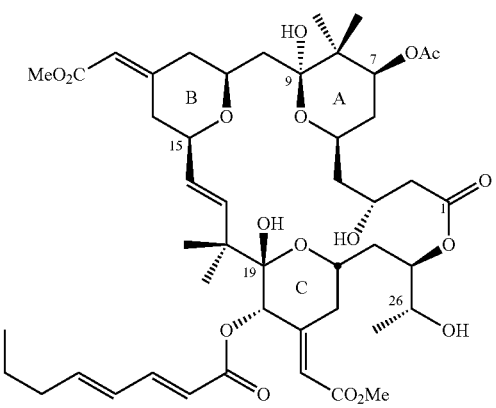

Bryostatin 1; $K_i$ = 1.35 nM

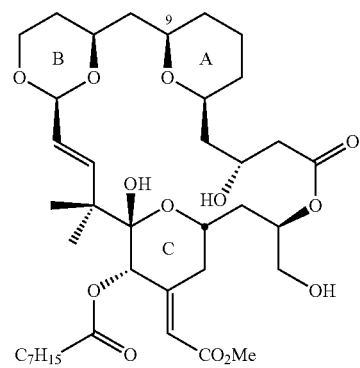

Analog 1; $K_i$ = 0.25 nM

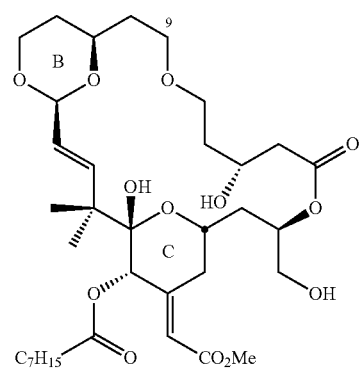

Analog 2; $K_i$ = 8.0 nM

-continued

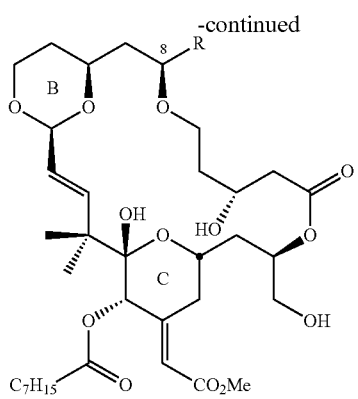

3 R = t-Bu
4 R = Ph
5 R = (CH2)3p-Br—Ph

B-ring bryologs may also be used in the present disclosure. These synthetic bryologs have affinities in the low nanomolar range. Wender et al., *Org Lett.* (2006), vol. 8, pp. 5299-5302, incorporated by reference herein in its entirety. B-ring bryologs have the advantage of being completely synthetic, and do not require purification from a natural source.

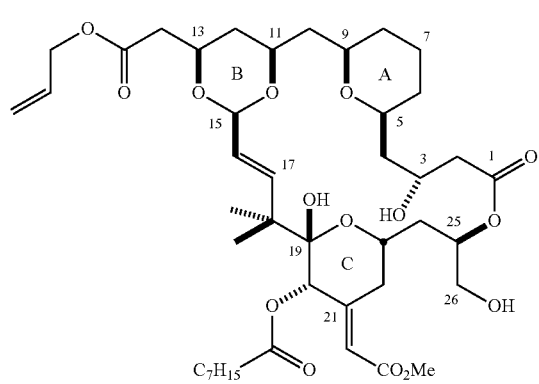

PKC $K_i$ = 1.2 ± 0.6 nM

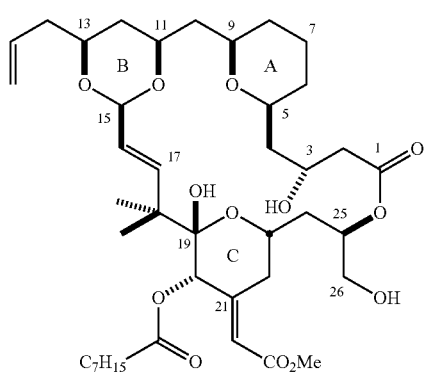

PKC $K_i$ = 0.67 ± 0.5 nM

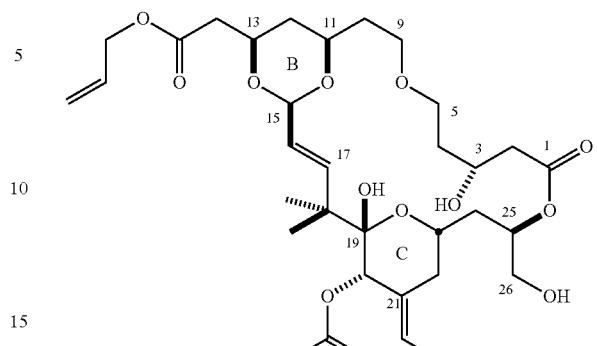

PKC $K_i$ = 3.0 ± 0.5 nM

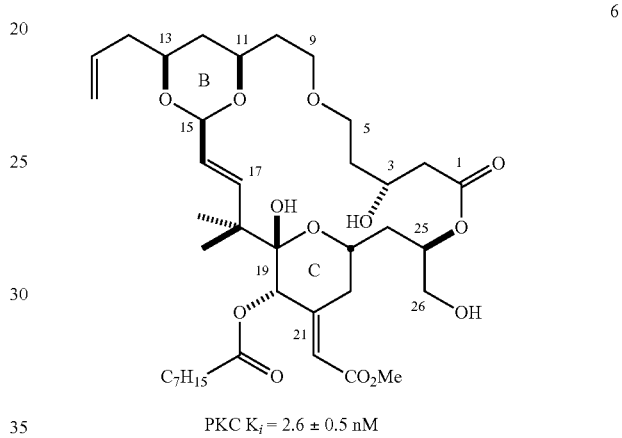

PKC $K_i$ = 2.6 ± 0.5 nM

A third class of suitable bryostatin analogs is the A-ring bryologs. These bryologs have slightly lower affinity for PKC than bryostatin-1 (6.5, nM, 2.3 nM, and 1.9 nM for bryologs 3, 4, and 5, respectively) and a lower molecular weight.

Bryostatin analogs are described in U.S. Pat. Nos. 6,624,189 and 7,256,286.

A number of derivatives of diacylglycerol (DAG) bind to and activate PKC. Niedel et al., *Proc. Natl. Acad. Sci.* (1983), vol. 80, pp. 36-40; Mori et al., *J. Biochem.* (1982), vol. 91, pp. 427-431; Kaibuchi et al., *J. Biol. Chem.* (1983), vol. 258, pp. 6701-6704. However, DAG and DAG derivatives are of limited value as drugs. Activation of PKC by diacylglycerols is transient, because they are rapidly metabolized by diacylglycerol kinase and lipase. Bishop et al. *J. Biol. Chem.* (1986), vol. 261, pp. 6993-7000; Chuang et al. *Am. J. Physiol.* (1993), vol. 265, pp. C927-C933; incorporated by reference herein in their entireties. The fatty acid substitution determines the strength of activation. Diacylglycerols having an unsaturated fatty acid are most active. The stereoisomeric configuration is important; fatty acids with a 1,2-sn configuration are active while 2,3-sn-diacylglycerols and 1,3-diacylglycerols do not bind to PKC. Cis-unsaturated fatty acids may be synergistic with diacylglycerols. In at least one embodiment, the term "PKC activator" expressly excludes DAG or DAG derivatives.

Isoprenoids are PKC activators also suitable for the present disclosure. Farnesyl thiotriazole, for example, is a synthetic isoprenoid that activates PKC with a $K_d$ of 2.5 Farnesyl thiotriazole, for example, is equipotent with dioleoylglycerol, but does not possess hydrolyzable esters of fatty acids. Gilbert et al., *Biochemistry* (1995), vol. 34, pp. 3916-3920; incorporated by reference herein in its entirety. Farnesyl thiotriazole and related compounds represent a stable, persistent PKC activator. Because of its low molecular weight (305.5 g/mol) and absence of charged groups, farnesyl thiotriazole would be expected to readily cross the blood-brain barrier.

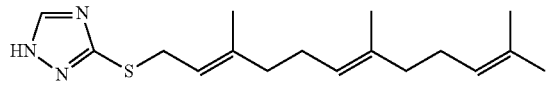 [SMILES: CC(C)=CCC/C(C)=C/CC/C(C)=C/CSc1nc[nH]n1]

Octylindolactam V is a non-phorbol protein kinase C activator related to teleocidin. The advantages of octylindolactam V (specifically the (−)-enantiomer) include greater metabolic stability, high potency ($EC_{50}$=29 nM) and low molecular weight that facilitates transport across the blood brain barrier. Fujiki et al. *Adv. Cancer Res.* (1987), vol. 49 pp. 223-264; Collins et al. *Biochem. Biophys. Res. Commun.* (1982), vol. 104, pp. 1159-4166, each incorporated by reference herein in its entirety.

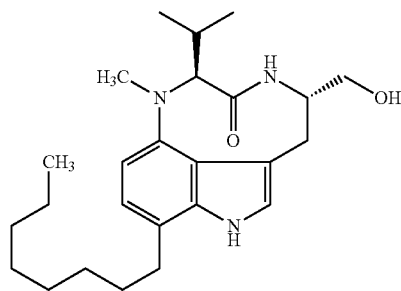 [SMILES: CCCCCCCCc1ccc2c3c(c[nH]c13)C[C@@H](CO)NC(=O)[C@H](C(C)C)N2C]

Gnidimacrin is a daphnane-type diterpene that displays potent antitumor activity at concentrations of 0.1 nM-1 nM against murine leukemias and solid tumors. It acts as a PKC activator at a concentration of 0.3 nM in K562 cells, and regulates cell cycle progression at the G1/S phase through the suppression of Cdc25A and subsequent inhibition of cyclin dependent kinase 2 (Cdk2) (100% inhibition achieved at 5 ng/ml). Gnidimacrin is a heterocyclic natural product similar to bryostatin, but somewhat smaller (MW=774.9 g/mol).

Iripallidal is a bicyclic triterpenoid isolated from *Iris pallida*. Iripallidal displays anti-proliferative activity in a NCI 60 cell line screen with $GI_{50}$ (concentration required to inhibit growth by 50%) values from micromolar to nanomolar range. It binds to PKCα with high affinity ($K_1$=75.6 nM). It induces phosphorylation of Erk1/2 in a RasGRP3-dependent manner. Its molecular weight is 486.7 g/mol. Iripallidal is about half the size of bryostatin and lacks charged groups.

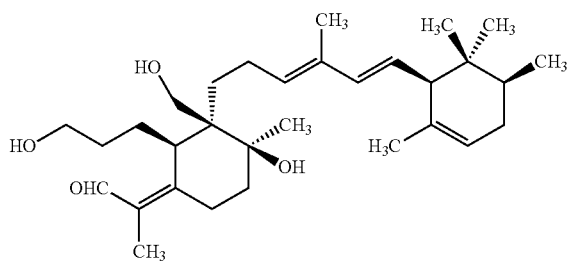

Ingenol is a diterpenoid related to phorbol but less toxic. It is derived from the milkweed plant *Euphorbia peplus*. Ingenol 3,20-dibenzoate, for example, competes with [3H] phorbol dibutyrate for binding to PKC ($K_1$=240 nM). Winkler et al., *J. Org. Chem.* (1995), vol. 60, pp. 1381-1390, incorporated by reference herein. Ingenol-3-angelate exhibits antitumor activity against squamous cell carcinoma and melanoma when used topically. Ogbourne et al. *Anticancer Drugs* (2007), vol. 18, pp. 357-362, incorporated by reference herein.

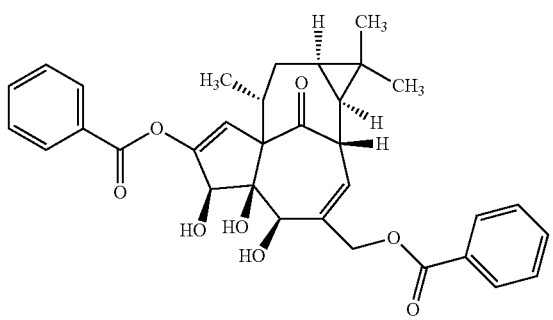 [SMILES: C[C@@H]1C[C@@H]2[C@H]([C@@H]3C=C(COC(=O)c4ccccc4)[C@@H](O)[C@]4(O)[C@@H](O)C(OC(=O)c5ccccc5)=CC14C3=O)C2(C)C]

Napthalenesulfonam ides, including N-(n-heptyl)-5-chloro-1-naphthalenesulfonamide (SC-10) and N-(6-phenylhexyl)-5-chloro-1-naphthalenesulfonamide, are members of another class of PKC activators. SC-10 activates PKC in a calcium-dependent manner, using a mechanism similar to that of phosphatidylserine. Ito et al., *Biochemistry* (1986), vol. 25, pp. 4179-4184, incorporated by reference herein. Naphthalenesulfonamides act by a different mechanism than bryostatin and may show a synergistic effect with bryostatin or member of another class of PKC activators. Structurally, naphthalenesulfonamides are similar to the calmodulin (CaM) antagonist W-7, but are reported to have no effect on CaM kinase.

Diacylglycerol kinase inhibitors may also be suitable as PKC activators in the present disclosure by indirectly activating PKC. Examples of diacylglycerol kinase inhibitors include, but are not limited to, 6-(2-(4-[(4-fluorophenyl) phenylmethylene]-1-piperidinyl)ethyl)-7-methyl-5H-thiazolo[3,2-a]pyrimidin-5-one (R59022) and [3-[2-[4-(bis-(4-fluorophenyl)methylene]piperidin-1-yl)ethyl]-2,3-dihydro-2-thioxo-4(1H)-quinazolinone (R59949).

A variety of growth factors, such as fibroblast growth factor 18 (FGF-18) and insulin growth factor, function through the PKC pathway. FGF-18 expression is up-regulated in learning, and receptors for insulin growth factor have been implicated in learning. Activation of the PKC signaling pathway by these or other growth factors offers an additional potential means of activating PKC.

Growth factor activators, including 4-methyl catechol derivatives like 4-methylcatechol acetic acid (MCBA) that stimulate the synthesis and/or activation of growth factors such as NGF and BDNF, also activate PKC as well as convergent pathways responsible for synaptogenesis and/or neuritic branching.

The PKC activators according to the present disclosure include fatty acids such as unsaturated fatty acids, e.g., MUFAs and/or PUFAs, and derivatives thereof in which at least one C=C double bond is replaced by a cyclopropyl group (i.e., "cyclopropanated" double bond) or an epoxyl group (i.e., "epoxidized" double bond). In some embodiments, all of the C=C double bonds of an unsaturated fatty acid are replaced by cyclopropyl groups and/or epoxyl groups. In some embodiments, the fatty acid derivatives may comprise both cyclopropyl groups and epoxyl groups.

In some embodiments of the present disclosure, the PKC activator comprises a fatty acid derivative to treat stroke. In some embodiments, for example, the fatty acid derivatives such as PUFA and/or MUFA derivatives may activate PKCε at low (e.g., nanomolar) concentrations.

The terminal functional group of the fatty acid derivatives may be, for example, a free carboxylic acid (—CO$_2$), an alcohol (—CHOH), or an ester (—CO$_2$R) such as a monoester or polyester. The alkyl group (R) of the ester may be straight or branched including, for example, methyl, ethyl, propyl, isopropyl, butyl, isobutyl, secbutyl, tert-butyl, pentyl, hexyl, heptyl, octyl, nonyl, decyl, undecyl, dodecyl, tridecyl, and tetradecyl groups. An ester may also be formed from a fatty acid linked to a fatty alcohol in an ester linkage. Other alkyl esters contemplated include aliphatic alcohol esters and aromatic alcohol esters. In one embodiment, for example, the alcohol ester is a propylene glycol ester. In another embodiment, the alcohol ester is a glycerol ester. Glycerol esters of fatty acids include, for example, glycerol fatty acid ester, glycerol acetic acid fatty acid ester, glycerol lactic acid fatty acid ester, glycerol citric acid fatty acid ester, glycerol succinic acid fatty acid ester, glycerol diacetyl tartaric acid fatty acid ester, glycerol acetic acid ester, polyglycerol fatty acid ester, and polyglycerol condensed ricinoleic acid ester. Glycerol derivatives are biologically important because fatty acids may be conjugated to glycerol in the form of phosphatidylcholine, phosphatidylserine, and phosphatidic acids. For example, triacylglycerols (or triglycerides) are compounds in which the carboxyl groups of three fatty acids are esterified to the hydroxyls of all three carbons of glycerol. Esterifying the carboxylic acid facilitates transport across the blood-brain barrier by eliminating the negative charge; an alcohol group also facilitates transport across the blood-brain barrier.

Figure 5:
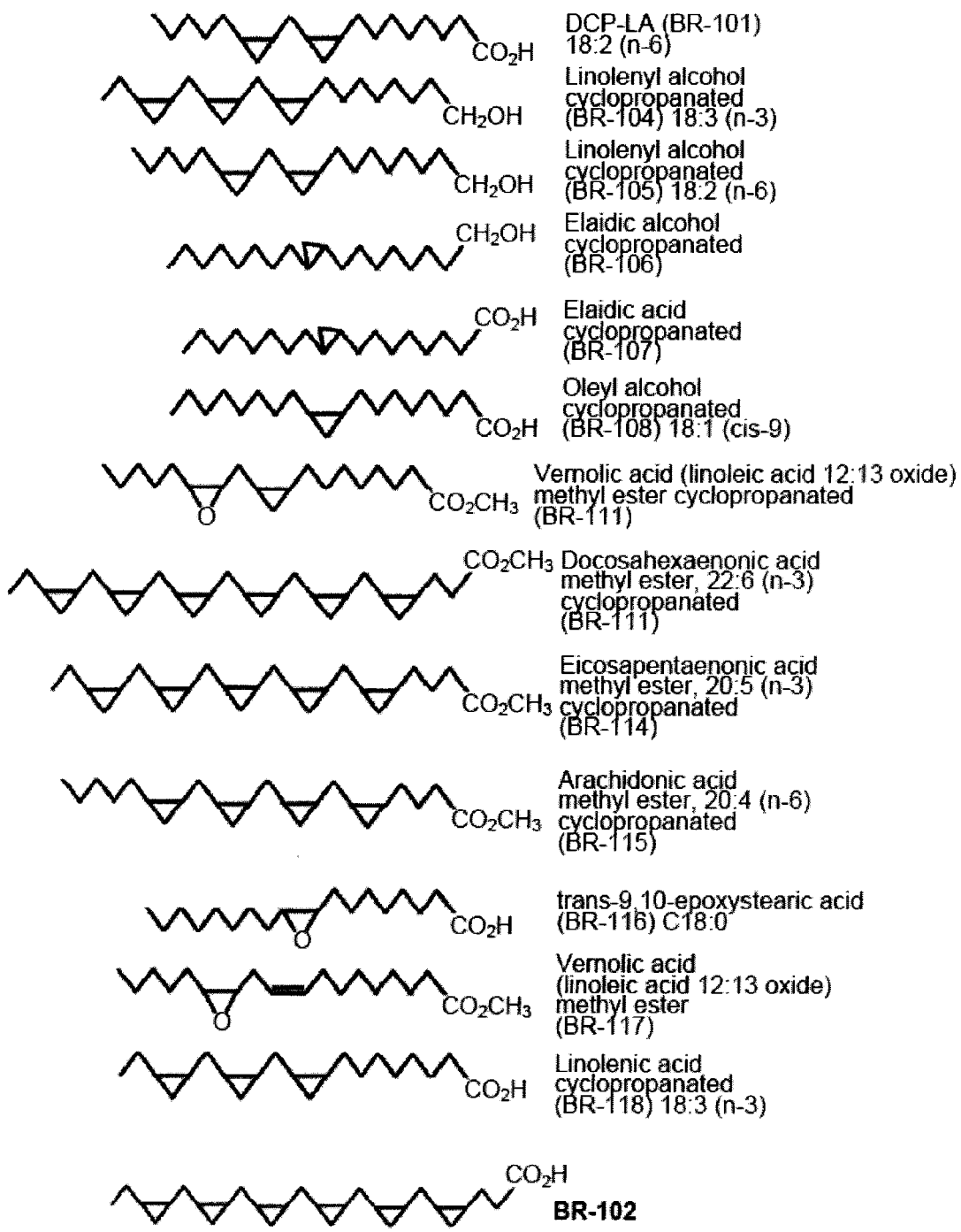
FIG. 5 shows the structures of various fatty acid derivatives according to the present disclosure (BR-101 through BR-118).

MUFAs that can be the basis for the fatty acid derivatives of the present disclosure include, but are not limited to, fatty acids with the following structure:

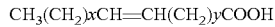

wherein each of x and y, independent of one another, is an odd integer from 3 to 11. Examples include cis- and trans-MUFAs such as oleic acid, elaidic acid, obtusilic acid, caproleic acid, lauroleic acid, linderic acid, myristoleic acid, palm itoleic acid, vaccenic acid, gadoleic acid, erucic acid, and petroselinic acid. Examples of MUFA alcohols include, for example, elaidic alcohol, oleyl alcohol, and 1-monolinoleyl rac-glycerol. Specific examples of cyclopropanated and epoxidized MUFA derivatives include eliadic alcohol cyclopropane (BR-106), eliadic acid cyclopropane (BR-107), oleyl alcohol cyclopropane (BR-108), and epoxystearic acid (BR-116). See FIG. 5.

Naturally cyclopropanated or epoxidized MUFAS or ester or alcohol derivatives thereof contemplated for the methods presently disclosed include malvenic acid, vernolic acid, and sterculic acid. An exemplary compound is vernolic acid methyl ester (BR-117).

PUFAs that can be the basis for fatty acid derivatives of the present disclosure include, but are not limited to, fatty acids with the following structure:

wherein x and y are each independently integers ranging from 2 to 6, including methylene- and/or polymethylene-interrupted polyenes. These are omega-6 PUFAs. Examples include, but are not limited to, linoleic acid, γ-linoleic acid, arachidonic acid, and adrenic acid, which have the following structures:

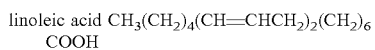

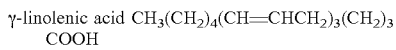

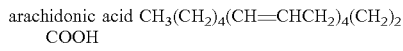

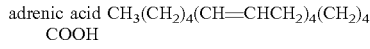

The linoleic acid derivative DCP-LA (2-[(2-pentylcyclopropyl)methyl]cyclopropaneoctanoic acid) (BR-101) is one of the few known isoform-specific activators of PKC known. See FIG. 5. DCP-LA selectively activates PKCε with a maximal effect at 100 nM. (Kanno et al., *J. Lipid Res.* (2006) vol. 47, pp. 1146-1156. Like SC-10, DCP-LA interacts with the phosphatidylserine binding site of PKC, instead of the diacylglycerol binding site.

Further examples of PUFAs that can be the basis for fatty acid derivatives of the present disclosure include the following structure:

wherein x and y are each independently integers ranging from 2 to 6, including methylene- and/or polymethylene-interrupted polyenes. These are omega-3 PUFAs. Examples include, but are not limited to, α-linoleic acid, docosahexaenoic acid, eicosapentaenoic acid, and eicosatetraenoic acid, which have the following structures:

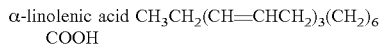

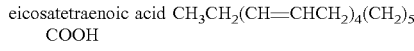

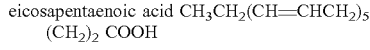

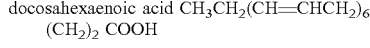

PUFA derivatives include PUFAs (carboxylic acid, alcohol, or ester terminal groups) wherein at least one of the C=C double bonds is cyclopropanated or epoxidized. Examples of cis-PUFA esters include the following structures:

where x and y are each independently integers ranging from 2 to 6, and R is an alkyl group. In some embodiments, R is the alkyl group of an alcohol such as a monohydric or polyhydric alcohol. Examples of alcohols include, but are not limited to, methanol, ethanol, propanol, butanol, pentanol, glycerol, mannitol, and sorbitol. In such cases, the alcohol may comprise a branched or unbranched alkyl chain or may comprise an aromatic alkyl such as a phenolic alcohol. Examples of PUFA derivatives include, but are not limited to, linoleic alcohol dicyclopropane (BR-105), linolenic alcohol tricyclopropane (BR-104), and vernolic acid methyl ester cyclopropane (BR-109). See FIG. 5.

In some embodiments, the PUFA derivative is a PUFA or ester or alcohol thereof wherein at least one of the C=C double bonds has been cyclpropanated or epoxidized. In some embodiments, for example, the PUFA derivative comprises a PUFA or ester or alcohol thereof with from two to six cyclopropanated or epoxidized double bonds. In at least one embodiment, the PUFA derivative comprises a PUFA or alcohol or ester thereof with three cyclopropanated or epoxidized double bonds. The PUFA derivatives of the present disclosure may also comprise both cyclopropyl groups and epoxyl groups.

In some embodiments, the PUFA derivative may comprise an epoxidized cis-PUFA alcohol such as linoleic alcohol dicyclopropane or linolenic alcohol tricyclopropane.

PUFAs that may form the basis of the cyclopropanated and/or epoxidized fatty acids according to the present disclosure include, but are not limited to, arachidonic acid (AA), docosahexaenoic acid (DHA), and eicosapentaenoic acid (EPA). Exemplary PUFA derivatives include docahexaenonic acid methyl ester hexacyclopropane (BR-111); eicosapentaenoic acid methyl ester pentacyclopropane (BR-114); and arachidonic acid methyl ester tetracyclopropane (BR-115). See FIG. 5.

In one embodiment, the PKC activator comprises a cyclopropanated PUFA derivative of DHA with the following structure:

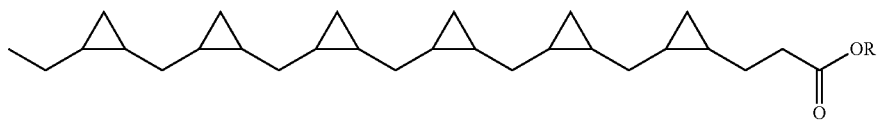

wherein R is H or an alkyl group. In one embodiment, R is methyl (BR-111 or DHA-CB6 methyl ester), or methyl-3-(2-((2-((2-((2-((2-((2-ethylcyclopropyl)methyl)cyclopropyl)methyl)cyclopropyl)methyl)-cyclopropyl)-cyclopropyl)methyl)cyclopropyl)methyl)cyclopropyl)propanoate.

In another embodiment, the PKC activator comprises a PUFA derivative with the following structure:

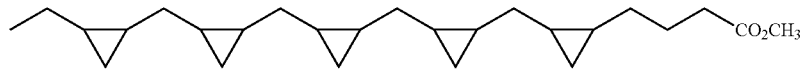

This compound is BR-114 (EPA-CP5 or methyl 4-(2((2-((2-((2-ethylcyclopropyl)methyl)cyclopropyl)methyl)cyclopropyl)methyl)cyclopropyl)methyl)-cyclopropyl)butanoate methyl ester).

In still another embodiment, the PKC activator comprises a PUFA derivative with the following structure:

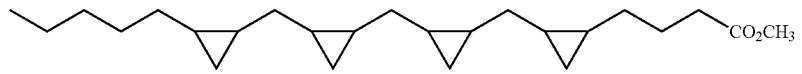 [SMILES: CCCCCC1CC1CC1CC1CC1CC1CC1CC1CCCC(=O)OC]

This compound is BR-115 (AA-CP4 or methyl 4-(2-((2-((2-((-pentylcyclopropyl)methyl)cyclopropyl)methyl)cyclopropyl)methyl)cyclopropyl)butanoate methyl ester).

In another embodiment, the PKC activator comprises a PUFA derivative with the following structure:

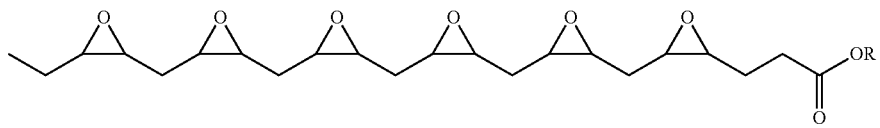

wherein R is H or an alkyl ester. In one embodiment, R is methyl.

Methods of Synthesis

Fatty acids, and esters and alcohols thereof, can be obtained or made from purification from natural sources, e.g., fish oil, flaxseed oil, soybeans, rapeseed oil, or algae, or synthesized using a combination of microbial enzymatic synthesis and chemical synthesis. As one example, fatty acid methyl esters can be produced by the transesterification of triglycerides of refined/edible type oils using methanol and an homogeneous alkaline catalyst.

Methods of cyclopropanation of double bonds in hydrocarbons are known in the art. For example, the modified Simmons-Smith reaction is a standard method for converting double bonds to cyclopropanes. Tanaka and Nishizaki, *Bioorg. Med. Chem. Lett.* (2003), vol. 13, pp. 1037-1040; Kawabata and Nishimura, *J. Tetrahedron* (1967), vol. 24, pp. 53-58; Denmark and Edwards, *J. Org. Chem.* (1991), vol. 56, pp. 6974-6981. In this reaction, treatment of alkenes with metal carbenoids, e.g., methylene iodide and diethylzinc, result in cyclopropanation of the alkene. See also Ito et al., *Organic Syntheses* (1988), vol. 6, p. 327. Cyclopropanation of methyl esters of was also effected using diazomethane in the presence of palladium (II) acetate as catalyst. Gangadhar et al., *J. Am. Oil Chem. Soc.* (1988), vol. 65, pp. 601-606.

Methods of epoxidation are also known in the art and typically involve reaction of fatty acid dioxiranes in organic solvents. Sonnet et al., *J. Am. Oil Chem. Soc.* (1995), vol. 72, pp. 199-204. As one example, epoxidation of PUFA double bonds can be achieved using dimethyldioxirane (OMD) as the epoxidizing agent. Grabovskiy et al., *Helvetica Chimica Acta* (2006) vol. 89, pp. 2243-22453.

The present disclosure contemplates treatment of neurological injuries and/or diseases associated with stroke. Without being limited to any particular mechanism, selective activation of PKCε may result in increased activation of alpha-secretase, e.g., tumor necrosis factor-α-converting enzyme (TACE), with a concomitant decrease in production of Aβ. However, this appears to occur mainly in non-neuronal cells such as fibroblasts. Activation of PKCε may also induce synaptogenesis or prevent apoptosis following stroke or in Alzheimer's disease. Activation of PKCε may also protect neurons from Aβ-mediated neurotoxicity through inhibition of GSK-3β.

The methods disclosed herein may reduce mortality 24 hours after stroke. For example, mortality after 24 hours may be reduced by at least 20%, at least 30%, at least 40%, or at least 50%. In at least one embodiment, the initial administration of a PKC activator and rTPA followed by subsequent administration of a PKC activator reduces mortality 24 hours after stroke by at least 40%.

In some embodiments, the methods of treatment disclosed herein may reduce disruption of the blood-brain barrier after stroke and/or may reduce hemorrhagic transformation. In some embodiments, for example, administering a PKC activator and rTPA after a stroke followed by subsequent administration of a PKC activator may reduce hemoglobin levels, wherein a reduction in hemoglobin indicates a reduction in hemorrhagic transformation and/or a reduction in disruption of the blood-brain barrier. In some embodiments, the hemoglovin level is reduced by about 30%, about 35%, about 40%, about 45%, about 50%, about 55%, or about 60%. In at least one embodiment, for example, the hemoglobin level is reduced by about 50%. Reduced disruption of the blood-brain barrier may also be assessed by measuring extravasation of albumin. DiNapoli et al., *Neurobiology of Aging* (2008), vol. 29, pp. 753-764.

Further, in some embodiments of the present disclosure, the size of the infarction due to stroke (e.g., tissue damage caused by an ischemic event) may be limited and/or reduced.

Formulation and Administration

The formulations of the pharmaceutical compositions described herein may be prepared by any suitable method known in the art of pharmacology. In general, such preparatory methods include bringing the active ingredient into association with a carrier or one or more other accessory ingredients, then, if necessary or desirable, shaping or packaging the product into a desired single- or multi-dose unit.

Although the descriptions of pharmaceutical compositions provided herein are principally directed to pharmaceutical compositions suitable for ethical administration to humans, it will be understood by skilled artisan that such compositions are generally suitable for administration to animals of all sorts. Modification of pharmaceutical compositions suitable for administration to humans order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

In some embodiments, the PKC activator and anticoagulant, e.g., rTPA, are formulated together. In other embodiments, the PKC activator and rTPA are formulated separately.

The compositions disclosed herein may be administered by any suitable route including oral, parenteral, transmucosal, intranasal, inhalation. or transdermal routes. Parenteral routes include intravenous, intra-arteriolar, intramuscular, intradermal, subcutaneous, intraperitoneal, intraventricular, intrathecal, and intracranial administration. A suitable route of administration may be chosen to permit crossing the blood-brain barrier. Rapoport et al., *J. Lipid Res*. (2001) vol. 42, pp. 678-685.

The compositions disclosed herein may be formulated according to conventional methods, and may include any pharmaceutically acceptable additives, such as excipients, lubricants, diluents, flavorants, colorants, buffers, and disintegrants. See e.g., Remington's Pharmaceutical Sciences, $20^{th}$ Ed., Mack Publishing Co. 2000.

In some embodiments, the PKC activator is formulated in a solid oral dosage form. For oral administration, the composition may take the form of a tablet or capsule prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods generally known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-phydroxybenzoates or sorbic acid). The preparations may also comprise buffer salts, flavoring, coloring and sweetening agents as appropriate.

In other embodiments of the present disclosure, the PKC activator may be formulated for parenteral administration such as bolus injection or continuous infusion. Formulations for injection may be presented in unit dosage form, e.g., in ampoules or in multi-dose containers, with an added preservative. The compositions may take such forms as suspensions, solutions, dispersions, or emulsions in oily or aqueous vehicles, and may contain formulatory agents such as suspending, stabilizing and/or dispersing agents.

In some embodiments, the PKC activator may be formulated with a pharmaceutically-acceptable carrier for administration. Pharmaceutically acceptable carriers include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are generally known in the art and may be described, for example, in *Remington's Pharmaceutical Sciences*, Genaro, ed., Mack Publishing Co., Easton, Pa., 1985, incorporated by reference herein.

In some embodiments, the PKC activator may be formulated with a hydrophobic carrier for administration. Hydrophobic carriers include inclusion complexes, dispersions (such as micelles, microemulsions, and emulsions), and liposomes. Exemplary hydrophobic carriers include inclusion complexes, micelles, and liposomes. See, e.g., Remington's: The Science and Practice of Pharmacy 20th ed., ed. Gennaro, Lippincott: Philadelphia, Pa. 2003. The PKC activators presently disclosed may be incorporated into hydrophobic carriers, for example as at least 1%, at least 5%, at least 10%, at least 20%, at least 30%, at least 40%, at least 50%, at least 60%, at least 70%, at least 80%, or at least 90% of the total carrier by weight. In addition, other compounds may be included either in the hydrophobic carrier or the solution, e.g., to stabilize the formulation.

In some embodiments, the PKC activator may also be formulated as a depot preparation. Such long acting formulations may be administered by implantation (for example subcutaneously or intramuscularly) or by intramuscular injection. Thus, for example, the PKC activator may be formulated with suitable polymeric or hydrophobic materials (for example as an emulsion in an acceptable oil) or ion exchange resins, or as sparingly soluble derivatives, for example, as a sparingly soluble salt.

In another embodiment, the PKC activator may be delivered in a vesicle, such as a micelle, liposome, or an artificial low-density lipoprotein (LDL) particle. See, e.g., U.S. Pat. No. 7,682,627.

The doses for administration may suitably be prepared so as to deliver from about 1 mg to about 10 g, such as from about 10 mg to about 1 g, or for example, from about 250 mg to about 500 mg of the PKC activator per day. When prepared for topical administration or parenteral formulations they may be made in formulae containing from about 0.01% to about 60% by weight of the final formulation, such as from about 0.1% to about 30% by weight, such as from about 1% to about 10% by weight. A suitable dose can be determined by methods known in the art and according to clinically relevant factors such as the age of the patient.

In at least one embodiment, the PKC activator is formulated for intravenous administration. The PKC activator may be administered in a dose ranging from about 5 $\mu g/m^2$ to about 50 $\mu g/m^2$, for example from about 10 $\mu g/m^2$ to about 30 $\mu g/m^2$, or from about 25 $\mu g/m^2$ to about 50 $\mu g/m^2$. In some embodiments, for example, the initial administration of a PKC activator ranges from about 25 $\mu g/m^2$ to about 50 $\mu g/m^2$. In some embodiments, the subsequent administration of a PKC activator ranges from about 5 $\mu g/m^2$ to about 30 $\mu g/m^2$, for example about 10 $\mu g/m^2$, about 15 $\mu g/m^2$, or about 20 $\mu g/m^2$. In some embodiments, the PKC activator and rTPA are both formulated for intravenous administration. The rTPA may be formulated for intravenous administration of a dose of about 0.9 mg/kg. The PKC and rTPA may be formulated together for intravenous administration, or they may be formulated separately for intravenous administration.

Kits

The present disclosure further relates to kits that may be utilized for preparing and administering pharmaceutical compositions of an anticoagulant, e.g., rTPA, and a PKC activator disclosed herein to a subject in need thereof. The kits may also comprise devices such as syringes for administration of the pharmaceutical compositions described herein.

In some embodiments, the kits may comprise one or more vials, syringes, needles, ampules, cartridges, bottles or other such vessels for storing and/or subsequently mixing compositions of rTPA and PKC activator disclosed herein. In certain embodiments, the devices, syringes, ampules, cartridges, bottles or other such vessels for storing and/or subsequently mixing the compositions of rTPA and a PKC activator disclosed herein may, or may not have more than one chamber.

In still further embodiments, the compositions of rTPA and a PKC activator disclosed herein may be stored in one or more graduated vessels (such as a syringe or syringes or other device useful for measuring volumes).

In certain embodiments, the kits may comprise pharmaceutical compositions of rTPA and a PKC activator stored within the same or separate ampules, vials, syringes, cartridges, bottles or other such vessels.

The kits may also comprise one or more anesthetics, preferably local anesthetics. In certain embodiments, the anesthetics are in a ready-to-use formulation, such as, for example an injectable formulation (optionally in one or more pre-loaded syringes) or a formulation that may be applied topically to an area where the compositions of rTPA and PKC activator disclosed herein are to be administered.

Topical formulations of anesthetics may be in form an anesthetic applied to a pad, swab, towelette, disposable napkin, cloth, patch, bandage, gauze, cotton ball, Q-tip™, ointment, cream, gel, paste, liquid, or any other topically applied formulation. Anesthetics for use with the present invention may include, but are not limited to lidocaine, marcaine, cocaine and xylocaine, for example.

The kits may also contain instructions relating to the use of the pharmaceutical compositions of rTPA and a PKC activator and procedures for mixing, diluting or combining formulations of rTPA and a PKC activator. The instructions may also contain directions for properly diluting formulations of rTPA and/or a PKC activator to obtain a desired pH or range of pHs and/or a desired specific activity and/or protein concentration after mixing but prior to administration. The instructions may also contain dosing information. The instructions may also contain material directed to methods for selecting subjects for treatment with the disclosed pharmaceutical compositions of rTPA and a PKC activator. The kits may also include additional buffers, syringes, needles, needle-less injection devices, sterile pads or swabs.

In some embodiments of the present disclosure, the kit comprises a composition comprising rTPA and one or more compositions comprising a PKC activator, for example at least two compositions each comprising a PKC activator. The two or more compositions may comprise the same or different PKC activators, and may be formulated for the same dose or different doses of PKC activator.

The following examples are intended to illustrate the present disclosure without, however, being limiting in nature. It is understood that the skilled artisan will envision additional embodiments consistent with the disclosure provided herein.

EXAMPLES

Example 1: Focal Ischemia Model of Stroke

A transient animal model of focal ischemia was used for these experiments. The middle cerebral artery (MCA) was surgically dissected and occluded in anesthetized rats by ligature, followed by reperfusion after a defined period (about 2 hours). Animal models transient ischemia via occlusion of the MCA (MCAO) are well-known and described in, e.g., Sicard and Fisher, *Exp. & Transl. Stroke Med.* (2009), vol. 1, pp. 1-7.

Example 2: Drug Administration

In a first experiment, rTPA was administered intravenously (~0.9 mg/kg) 6 hours after the ischemic event, followed 2 hours later with a single intravenous administration of bryostatin-1 in a dosage range of from about 25 μg/m² to 50 μg/m².

In a second experiment, bryostatin-1 was administered intravenously (about 25 μg/m² to 50 μg/m²) 2 hours after the ischemic event, followed by intravenous administration of rTPA (~0.9 mg/kg) about 6 hours later.

In a third experiment, rTPA was administered intravenously (~0.9 mg/kg) 2 hours after the ischemic event, followed by intravenous administration of bryostatin-1 in a dosage range of from about 25 μg/m² to 50 μg/m² about 6 hours later.

Example 3: Results

1. Mortality.

rTPA given 6 hours after the stroke, followed 2 hours later with bryostatin-1 led to 0% mortality 24 hours later (N=9 animals). In contrast, if rTPA was given 6 hours after the stroke, in the absence of subsequent treatment with bryostatin, 44% mortality was observed (N=6 animals).

2. Hemorrhage, Edema, and Blood-Brain Barrier Disruptions.

Figure 2:
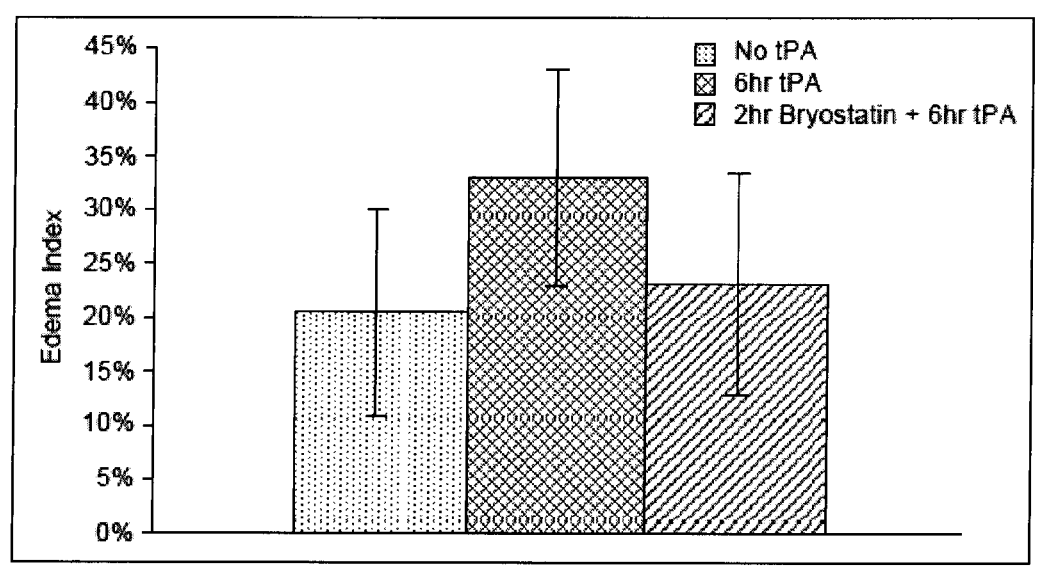
FIG. 2 shows a the percent of brain edema following ischemic stroke in rats treated with either rTPA at 6 hours following the stroke, or a combination of bryostatin-1 administered 2 hours after the stroke, followed 6 hours later by rTPA.

Bryostatin-1 administered 2 hours after the stroke, followed 6 hours later by rTPA, resulted in a 50% reduction of assayed hemoglobin in the cortex and striatum, as compared to rTPA given 6 hours after the stroke without prior bryostatin-1 treatment (FIG. 1). Brain edema was also significantly reduced with this combination of rTPA and bryostatin-1 (FIG. 2).

Figure 3:
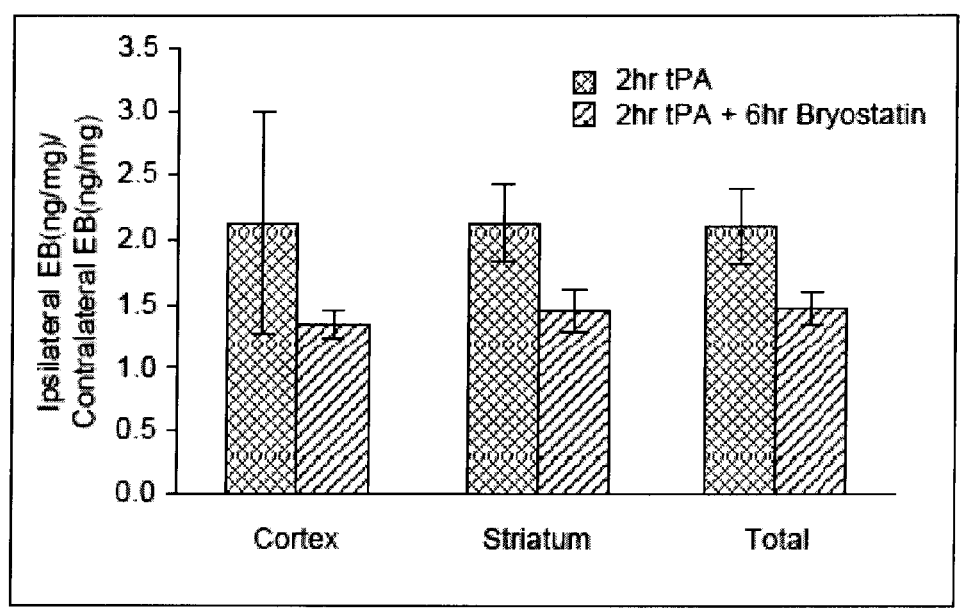
FIG. 3 shows the results of uptake of Evans Blue dye in the ipsilateral and contralateral cortices in rats treated with rTPA 2 hours following the stroke, or a combination of rTPA at 2 hours followed 6 hours later with bryostatin-1.

The BBB permeability typically increase prior to the occurrence of edema following focal ischemia, such that edema can be used to measure BBB disruptions at the site of the ischemic lesion. In addition, the hemorrhage process is involved in the BBB disruption and edema. In one experiment, uptake of Evans Blue dye was used to measure BBB permeability, i.e., disruption, and hemorrhaging in ischemic animal models of stroke. FIG. 3 shows that combinations of bryostatin and administered according to the methods of the present disclosure significantly reduced uptake of Evans Blue dye in the ipsilateral and contralateral cortices.

Figure 4:
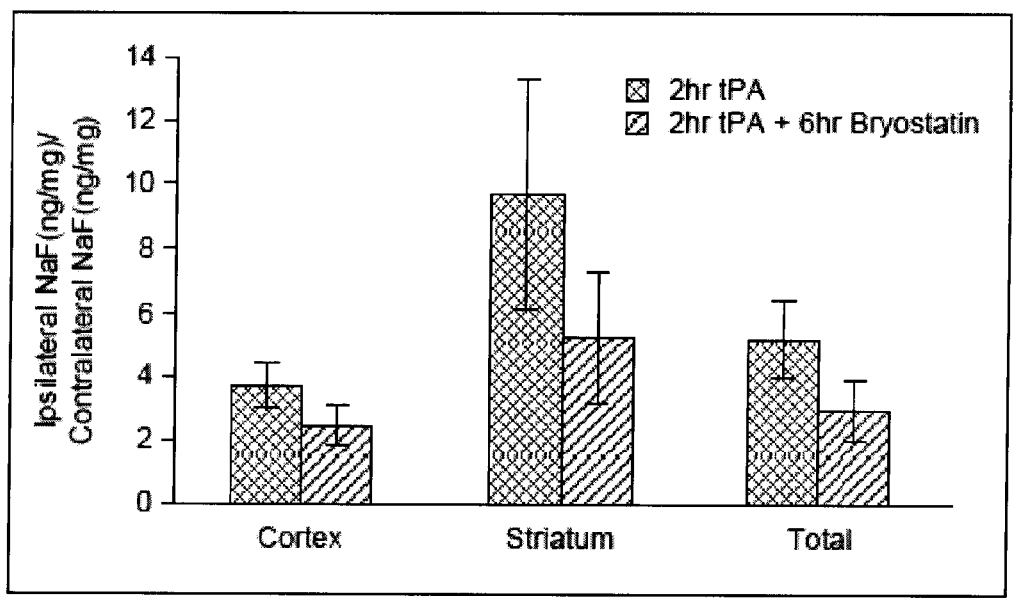
FIG. 4 shows the results of sodium fluoride uptake in the ipsilateral and contralateral cortices in rats treated with rTPA 2 hours following the stroke, or a combination of rTPA at 2 hours followed 6 hours later with bryostatin-1.

Lastly, increased transport of sodium across the (BBB) contributes to cerebral edema formation in ischemic stroke. FIG. 4 shows that uptake of NaF in the ipsilateral and contralateral cortices is also reduced with the disclosed administration regimens of bryostatin-1 and rTPA.

The foregoing results demonstrate that the combination of bryostatin-1 with rTPA following ischemic stroke unexpectedly and significantly reduces mortality and brain injury following ischemic stroke.

Example 4: Synthesis of Fatty Acid Methyl Esters Cyclopropanated Fatty Acid Methyl Esters Synthesis of cyclopropanated fatty acids. Methyl esters of PUFAs were cyclopropanated using the modified Simmons-Smith reaction using chloroiodomethane and diethylzinc. Tanaka et al., *Bioorg. Med. Chem. Lett.* (2003), vol. 13, pp. 1037-1040; Furukawa et al., *Tetrahedron* (1968), vol. 24, pp. 53-58; Denmark et al., *J. Org. Chem.* (1991), vol. 56, pp. 6974-6981. All apparatus were baked at 60° C. for 1 hr and dried using a flame with dry nitrogen. A 100 ml 3-neck round bottom flask with a stirring bar and a temperature probe was surrounded by an ice-dry ice mixture and filled with 1.25 g (4.24 mmol) linoleic acid methyl ester or docosahexaenoic acid methyl ester in 25 ml dichloromethane and bubbled with $N_2$. A 1M solution of diethylzinc (51 ml, 54.94 mmol) hexane was added anaerobically using a 24-inch-long 20-gauge needle and the solution was cooled to −5° C. Diiodomethane (8.2 ml, 101.88 mmol) or chloroiodomethane ($ClCH_2I$) was added dropwise, one drop per second, with constant stirring. The rate of addition was decreased if necessary to maintain the reaction mixture below 2° C. The reaction mixture became cloudy during the reaction and an insoluble white zinc product was liberated. The flask was sealed and the mixture was allowed to react for 1 hr and then allowed to come to room temperature gradually over 2 hr.

To prevent the formation of an explosive residue in the hood, diethylzinc was not evaporated off. The mixture was slowly poured into 100 ml of water under stirring to decompose any excess diethylzinc. Ethane was evolved. The mixture was centrifuged at 5000 rpm in glass centrifuge tubes and the upper aqueous layer discarded.

The white precipitate was extracted with $CH_2Cl_2$ and combined with the organic phase. The organic phase was washed with water and centrifuged. The product was analyzed by silica gel G TLC using hexane plus 1% ethyl acetate and purified by chromatography on silica gel using increasing concentrations of 1-10% ethyl acetate in n-hexane and evaporated under nitrogen, leaving the methyl ester as a colorless oil.

The Simmons-Smith reaction preserves the stereochemistry of the starting materials. Furukawa et al., *Tetrahedron* (1968), vol. 24, pp. 53-58. Docosahexaenoic acid methyl ester was converted into DHA-CP6 in 90-95% yield. The product was a colorless oil with a single absorbance maximum at 202 nm in ethanol and no reaction with $I_2$. The IR spectrum showed cyclopropane ring absorption at 3070 $cm^{-1}$ and 1450 $cm^{-1}$. Under the same conditions, eicosapentaenoic acid methyl ester was converted to EPA-CP5, and arachidonic acid methyl ester was converted to AA-CP4. Linoleic acid methyl ester was converted to DCP-LA methyl ester which was identical to a known sample.

Hydrolysis of methyl ester. The methyl ester (0.15 g) was dissolved in 1 ml 1N LiOH and 1 ml dioxane. Dioxane and methanol were added until it became homogeneous and the solution was stirred at 60° C. overnight. The product was extracted in $CH_2Cl_2$ and centrifuged. The aqueous layer and white interface were re-extracted with water and washed until the white layer no longer formed. The product was evaporated under $N_2$ and purified by chromatography on silica gel. The product, a colorless oil, eluted in 20% EtOAc in n-hexane. Its purity was checked by TLC in 10% EtOAc/hexane and by C18 RP-HPLC using UV detection at 205 nm.

The epoxide groups can be introduced by conventional means, e.g., by oxidation of the appropriate alkene with m-chloroperbenzoic acid or t-butylhydroperoxide. Other compounds synthesized include those shown in FIG. 5 (BR-101 through BR-118).

Example 5: Activation of Purified PKCϵ Using Docosahexanoic Acid

PKC assay. Recombinant PKC (1 ng of PKCα or PKCϵ isoform) was mixed with BR-101 (DCP-LA) in the presence of 10 micromolar histones, 5 mM $CaCl_2$, 1.2 µg/µl phosphatidyl-L-serine, 0.18 µg/µl 1,2-dioctanoyl-sn-glycerol (DAG), 10 mM $MgCl_2$, 20 mM HEPES (pH 7.4), 0.8 mM EDTA, 4 mM EGTA, 4% glycerol, 8 µg/ml aprotinin, 8 µg/ml leupeptin, and 2 mM benzamidine. 0.5 micro $Ci[\gamma^{32}P]$ ATP was added. The incubation mixture was incubated for 15 min at 37 degrees in a total volume of 10 microliters. The reaction was stopped by spotting the reaction mixtures on 1×2 cm strips of cellulose phosphate paper (Whatman P81) and immediately washing twice for 1 hr in 0.5% $H_3PO_4$. The cellulose phosphate strips were counted in a scintillation counter. In some experiments, phosphatidylserine, diacylglycerol, and/or calcium were removed.

DHA methyl ester was purchased from Cayman Chemical (Ann Arbor, Me.). PKC isozymes were from Calbiochem (San Diego, Calif.). Purified PKCϵ was purchased from Calbiochem.

Results

Figure 6:
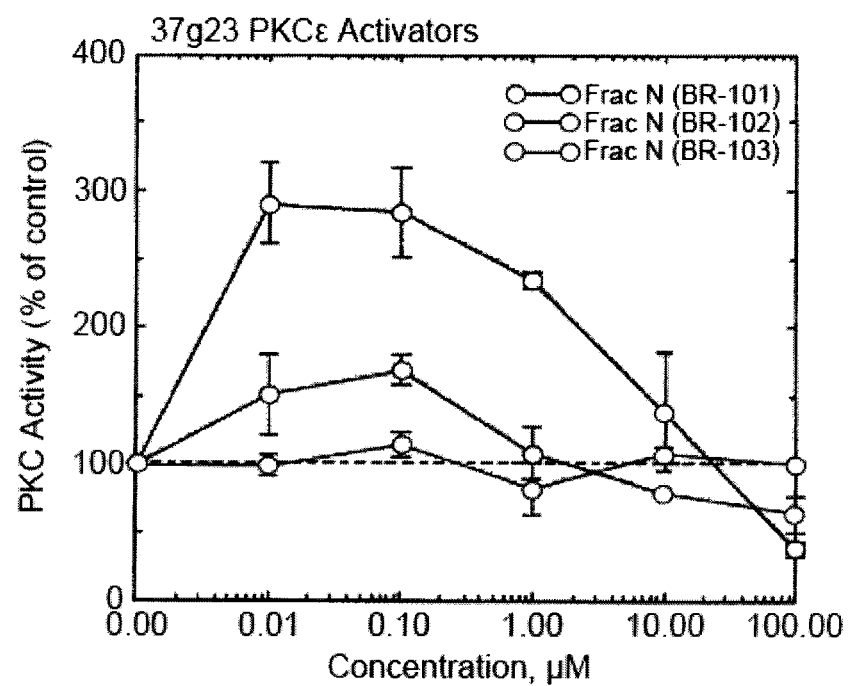
FIG. 6 shows PKCε activation by BR-101 (DCP-LA), BR-102, and BR-103.

PKC measurements using purified PKCϵ showed that, at the lowest concentration tested (10 nM), compound BR-101 produced a 2.75-fold activation of PKCϵ (FIG. 6). PKCα was not affected (data not shown). Compound BR-102 also selectively elicited activation of PKCϵ to about 1.75 fold over unactivated PKCϵ. The effectiveness of these compounds in activating PKCϵ at low concentrations suggests that they will be good therapeutic candidates.

Example 6: Activation of Purified or Cellular PKC Epsilon Using Other PKC Activators Materials. Culture media were obtained from K-D Medical (Columbia, Md.) or Invitrogen (Carlsbad, Calif.). Aβ1-42 was purchased from Anaspec (San Jose, Calif.). Polyunsaturated fatty acid methyl esters were obtained from Cayman Chemicals, Ann Arbor, Mich. Other chemicals were obtained from Sigma-Aldrich Chemical Co. (St. Louis, Mo.). PKC isozymes were from Calbiochem (San Diego, Calif.). Purified PKCϵ was purchased from Calbiochem.

Cell culture. Rat hippocampal H19-7/IGF-IR cells (ATCC, Manassas, Va.) were plated onto poly-L-lysine coated plates and grown at 35° C. in DMEM/10% FCS for several days until about 50% coverage was obtained. The cells were then induced to differentiate into a neuronal phenotype by replacing the medium with 5 ml $N_2$ medium containing 10 ng/ml basic fibroblast growth factor at 39° C. and grown in T-75 flasks at 37° C. Human SH-SY5Y neuroblastoma cells (ATCC) were cultured in 45% F12K/45% MEM/10% FCS. Mouse N2A neuroblastoma cells were cultured in DMEM/10% FCS without glutamine. Rat hippocampal neurons from 18-day-old embryonic Sprague Dawley rat brains were plated on 12- or 96-well plates coated with poly-D-lysine (Sigma-Aldrich, St. Louis, Mo.) in B-27 neurobasal medium containing 0.5 mM glutamine and 25 µM glutamate (Invitrogen, Carlsbad, Calif.) and cultured for three days in the medium without glutamate. The neuronal cells were grown under 5% $CO_2$ in an incubator maintained at 37° C. for 14 days.

All experiments on cultured cells were carried out in triplicate unless otherwise stated. All data points are displayed as mean±SE. BR-101 (DCP-LA) was used as its free acid all experiments, while BR-111 (DHA-CP6), BR-114 (EPA-CP5), and BR-116 (AA-CP4) were used as their methyl esters.

Protein kinase C assay. Rat hippocampal cells were cultured and scraped in 0.2 ml homogenization buffer (20 mM Tris-HCl, pH 7.4, 50 mM NaF, 1 µg/ml leupeptin, and 0.1 mM PMSF) and homogenized by sonication a Marsonix microprobe sonicator (5 sec, 10 W). To measure PKC, 10 µl of cell homogenate or purified PKC isozyme (purchased from Calbiochem) was incubated for 15 min at 37° C. in the presence of 10 µM histones, 4.89 mM $CaCl_2$, 1.2 µg/µl phosphatidyl-L-serine, 0.18 µg/µl 1,2-dioctanoyl-sn-glycerol, 10 mM $MgCl_2$, 20 mM HEPES (pH 7.4), 0.8 mM EDTA, 4 mM EGTA, 4% glycerol, 8 µg/ml aprotinin, 8 µg/ml leupeptin, and 2 mM benzamidine. 0.5 $Ci[\gamma^{32}P]ATP$ was added and $^{32}P$-phosphoprotein formation was measured by adsorption onto phosphocellulose as described previously. Nelson and Alkon, J. Neurochemistry (1995), vol. 65, pp. 2350-2357. For measurements of activation by BR-101 (DCP-LA) and similar compounds. PKC activity was measured in the absence of diacylglycerol and phosphatidylserine and PKC δ, ϵ, η, and µ were measured in the absence of added EGTA and $CaCl_2$, as described by Kanno et al. (J. Lipid Res. 2006, vol. 47, pp. 1146-1150). Low concentrations of $Ca^{2+}$ are used because high $Ca^{2+}$ interacts with the PKC phosphatidylserine binding site and prevents activation. For measurements of bryostatin activation, 1,2-diacylglycerol was omitted unless otherwise stated.

Results and Discussion

To determine their PKC isozyme specificity, fatty acid derivatives were preincubated with purified PKC for five minutes and the PKC activity was measured radiometrically. As shown for Example 5, above, BR-101 (DCP-LA) was an effective activator of PKCϵ at 10 µM but had relatively small effects on the other PKC isoforms (data not shown). At higher concentrations BR-101 (DCP-LA) partially inhibited PKCδ (about 1-100 µM) and activated PKCγ (50-100 µM) (data not shown).

Figure 7:
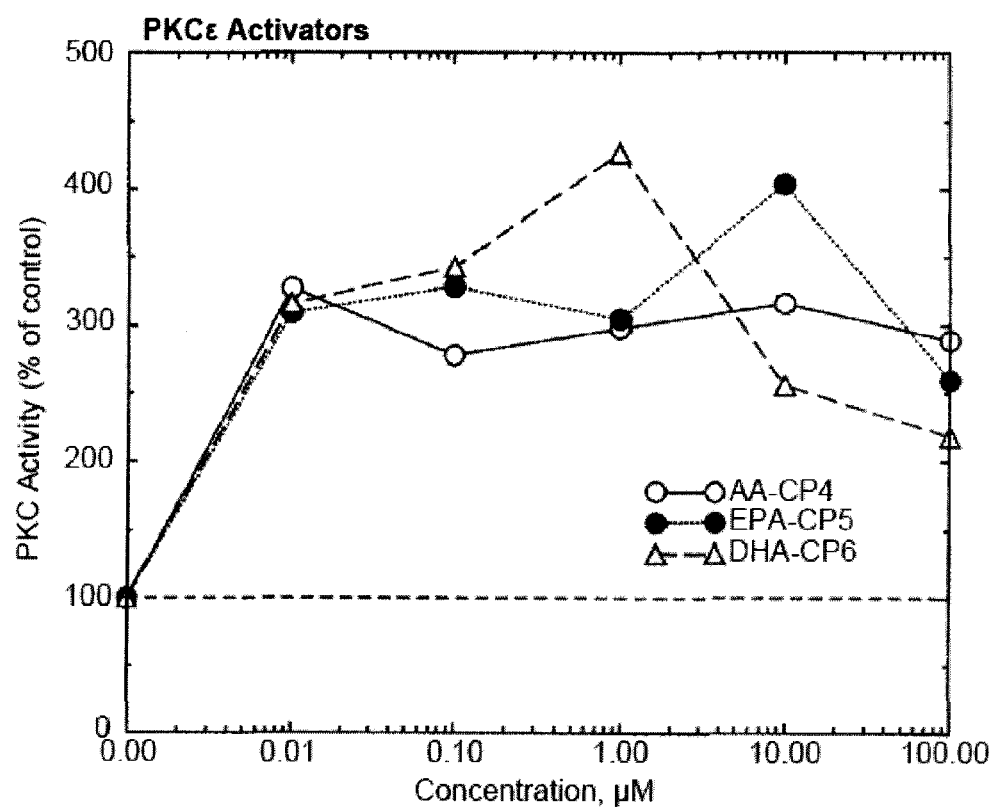
FIG. 7 shows PKCε activation by vanous concentrations of BR-111 (DHA-CP6 methyl ester), BR-114 (EPA-CP5 ester), and BR-115 (AA-CP4 methyl ester).
Figure 8:
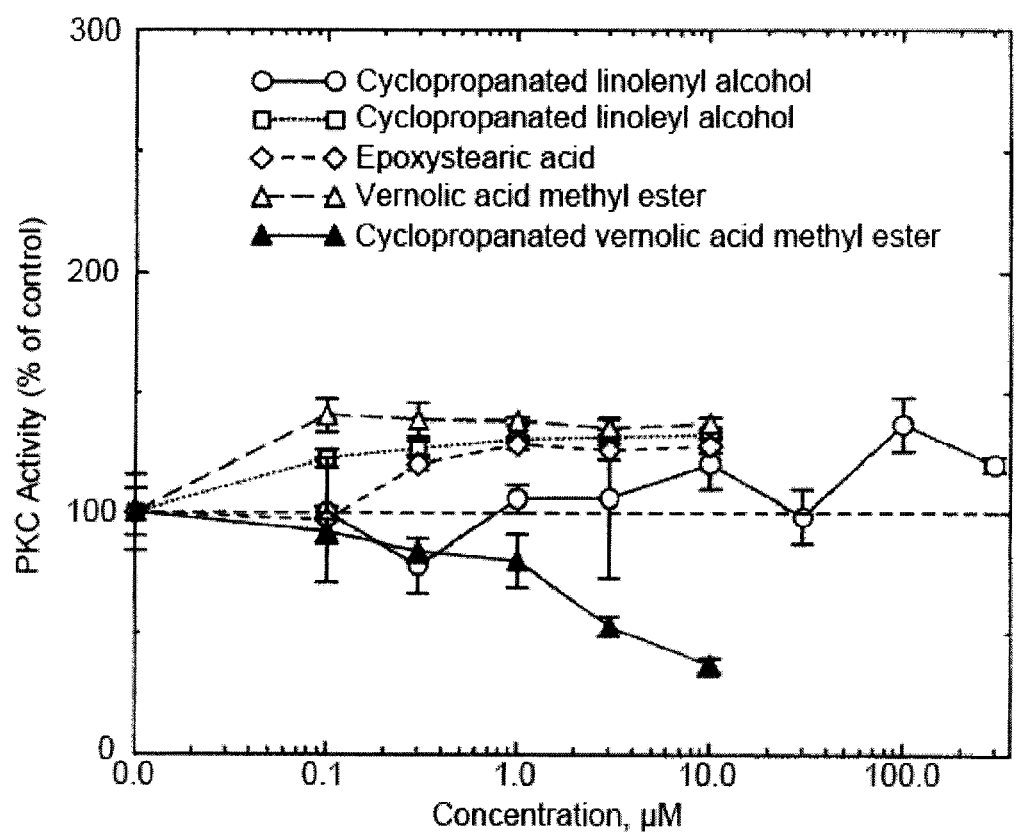
FIG. 8 shows PKCε activation by various concentrations of cyclopropanated and epoxidized fatty acid methyl esters: cyclopropanated linolenyl alcohol (BR-104); cyclopropanated linoleyl alcohol (BR-105); epoxystearic acid (BR-116); vernolic acid methyl ester (BR-117); and cyclopropanated vernolic acid methyl ester (BR-109).

BR-111 (DHA-CP6), BR-114 (EPA-CP5), and BR-115 (AA-CP4), the cyclopropanated derivatives of docosahexaenoic acid, eicosapentaenoic acid, and arachidonic acid, respectively, activated purified PKCϵ to a similar extent (FIG. 7) The concentration needed to activate PKC was approximately 100 times lower than for BR-101 (DCP-LA), suggesting higher affinity. Cyclopropanated linolenyl and linoleyl alcohols (BR-104 and BR-105), epoxystearic acid (BR-116), and vemolic acid methyl ester (BR-117) had little or no effect on PKC (FIG. 8). Cyclopropanated vemolic acid methyl ester (BR-109) inhibited PKCε at concentrations above 1 µM (FIG. 8).

Figure 9:
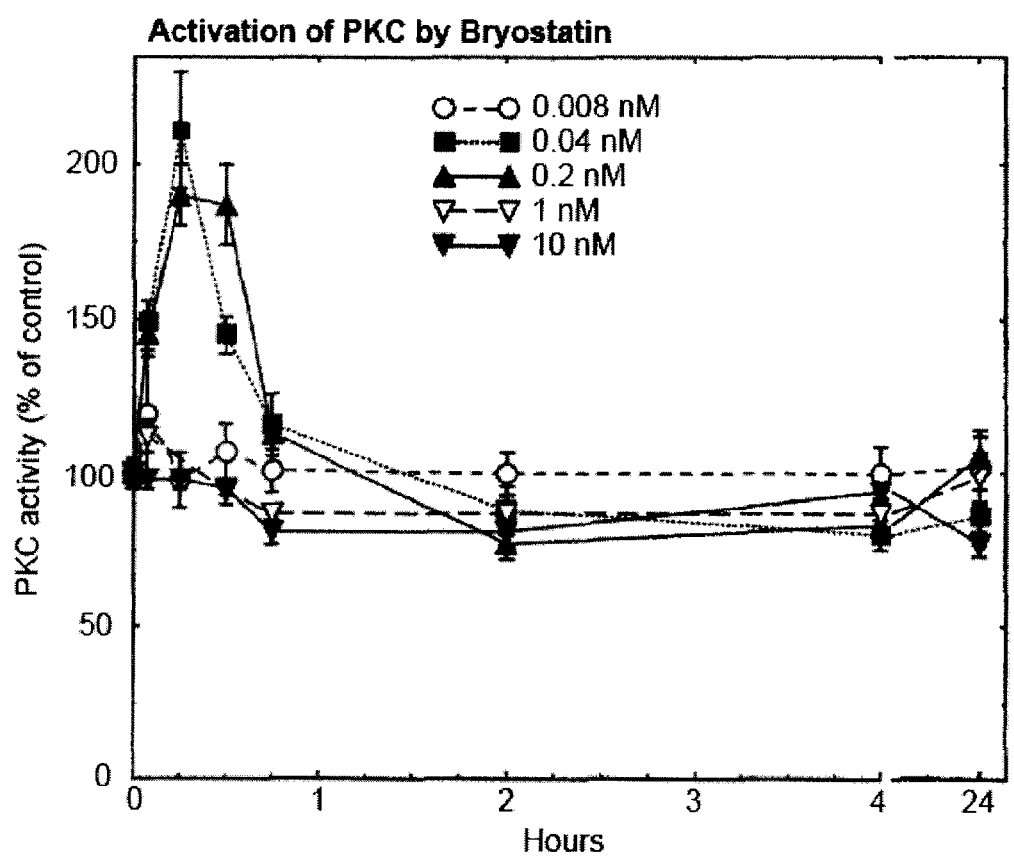
FIG. 9 shows PKC activation over time by various concentrations of bryostatin in H19-7/IGF-IR rat hippocampal neurons.
Figure 10:
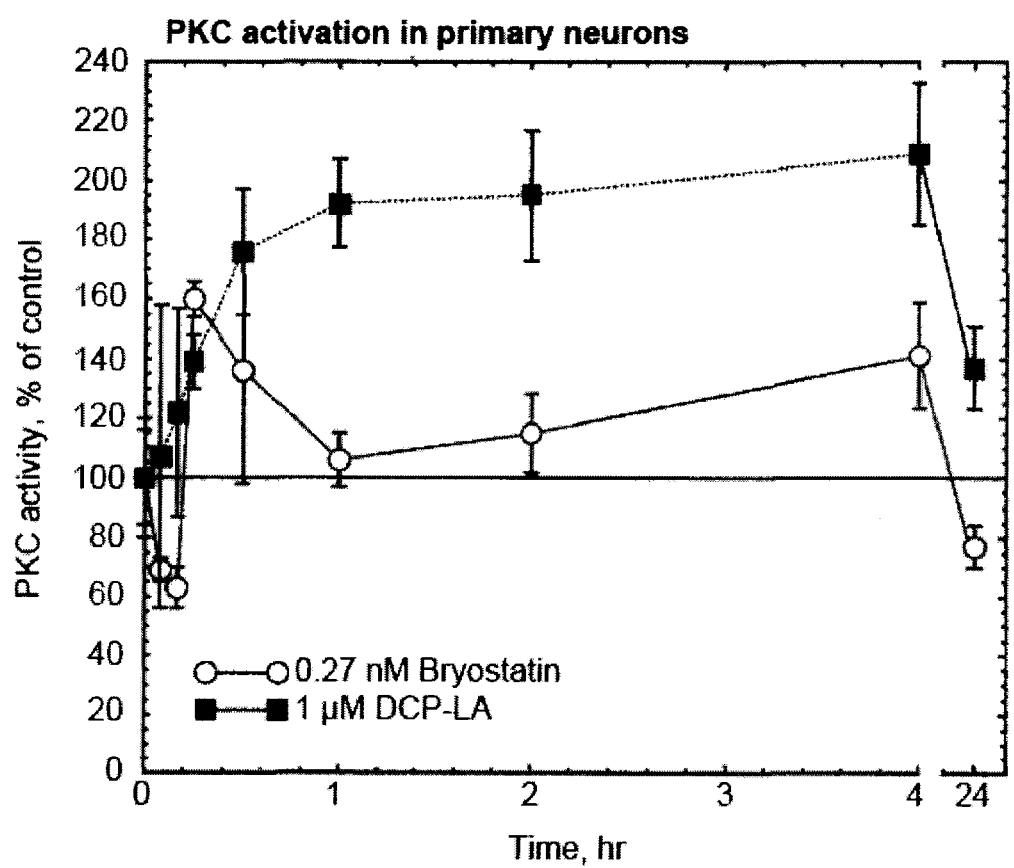
FIG. 10 shows PKC activation over time by bryostatin and DCP-LA in rat hippocampal primary neurons.

PKC activators that bind to the diacylglycerol binding site, including bryostatin, gnidimacrin, and phorbol esters, produce a transient activation of PKC activity, followed by a prolonged downregulation. Nelson et al., *Trends in Biochem. Sci.* (2009), vol. 34, pp. 136-145. This was confirmed in cultured rat hippocampal cells. Incubation of rat H19-7/IGF-IR cells with (0.04 nM and 0.2 nM) bryostatin produced a 2-fold activation that lasted 30 min, followed by a 20% downregulation that returned to baseline by 24 hours (data not shown). In contrast, PKC exposed to DCP-LA remained elevated for at least four hours (FIG. 9). This sustained activation was only observed in primary neurons.

Even though bryostatin has a higher affinity for PKC than phorbol 12-myristate 13-acetate (PMA) (EC50=1.35 nM vs. 10 nM), bryostatin was much less effective than PMA at downregulating PKC. PKC activity is strongly downregulated by phorbol ester at 8 hours, while PKC in bryostatin-treated cells is at or near the baseline (data not shown). This difference may explain the increases in Aβ produced by PdBu reported by da Cruz e Silva et al. *J. Neurochem.* (2009), vol. 108, pp. 319-330. These investigators applied 1 µM PdBu to cultured COS cells for 8 hours and observed an increase in Aβ. This increase was attributed to downregulation of PKC by the phorbol ester, which is consistent with these results. Downregulation could not be measured for DCP-LA and related compounds.

Example 7: Effects of PKC Activators on AR Production and Degradation

Cell culture. Cell culture was performed as described in Example 6.

Aβ Measurement and Cell Viability Assay. Aβ was measured using an Aβ 1-42 human fluorimetric ELISA kit (Invitrogen) according to the manufacturer's instructions. Results were measured in a Biotek Synergy HT microplate reader. AlamarBlue and CyQuant NF (Invitrogen) according to the manufacturer's instructions.

Results and Discussion

Figure 11A:
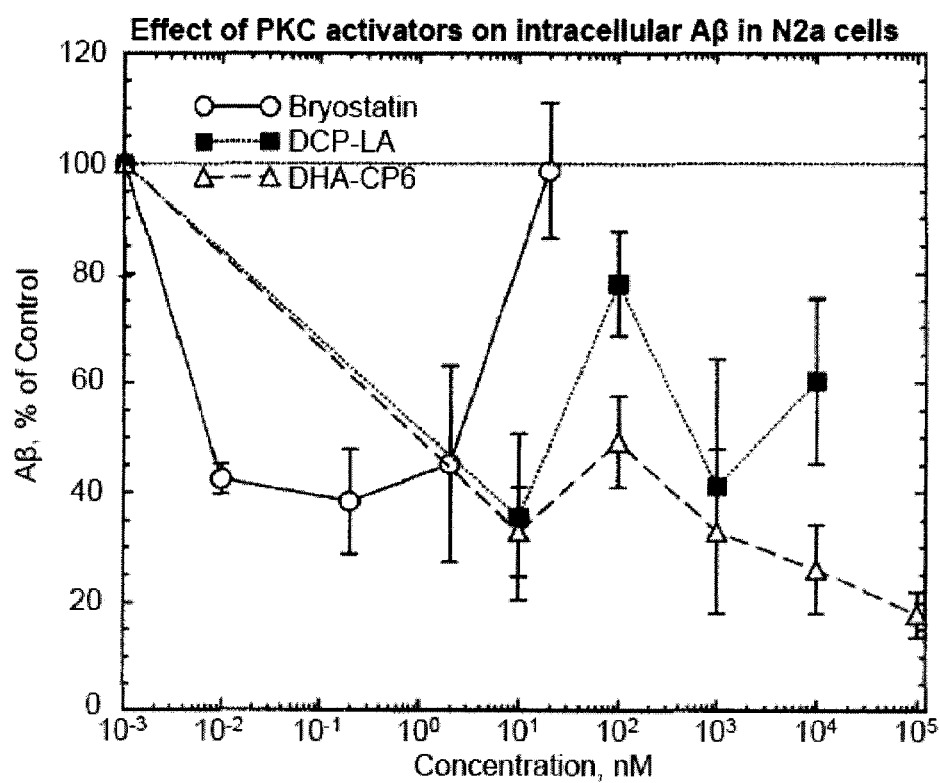
FIGS. 11a and 11b show levels of intracellular (FIG. 11a) and secreted (FIG. 11b) Aβ in neuro2a (N2A) cells exposed to bryostatin, BR-101 (DCP-LA), and BR-111 (DHA-CP6).
Figure 11B:
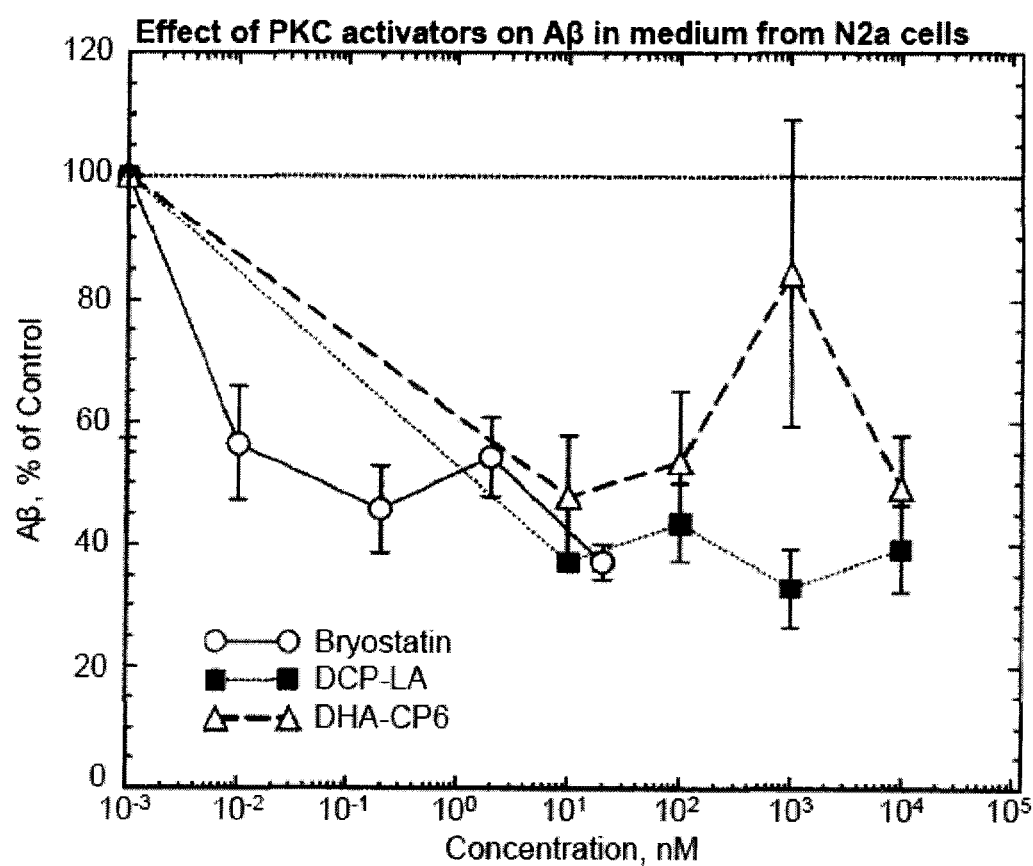

To measure the effects of PKCε activation on Aβ production, mouse neuro2a (N2a) neuroblastoma cells transfected with human APPSwe/PSID were used, which produce large quantities of Aβ. Petanceska et al., *J Neurochem.* (1996), vol. 74, pp. 1878-1884. Incubation of these cells for 24 hours with various concentrations of PKC activators bryostatin, BR-101 (DCP-LA) and BR-111 (DHA-CP6) markedly reduced the levels of both intracellular (FIG. 11a) and secreted (FIG. 11b) Aβ. With bryostatin, which activates PKC by binding to the diacylglycerol-binding site, the inhibition was biphasic with concentrations of 20 nM or higher producing no net effect. This may be explained by the ability of this class of PKC activators to downregulate PKC when used at high concentrations. In contrast, BR-101 (DCP-LA) and BR-111 (DHA-CP6), which bind to PKC's phosphatidylserine site, showed monotonically increasing inhibition at concentrations up to 10 µM to 100 µM with no evidence of downregulation at higher concentrations.

Figure 12:
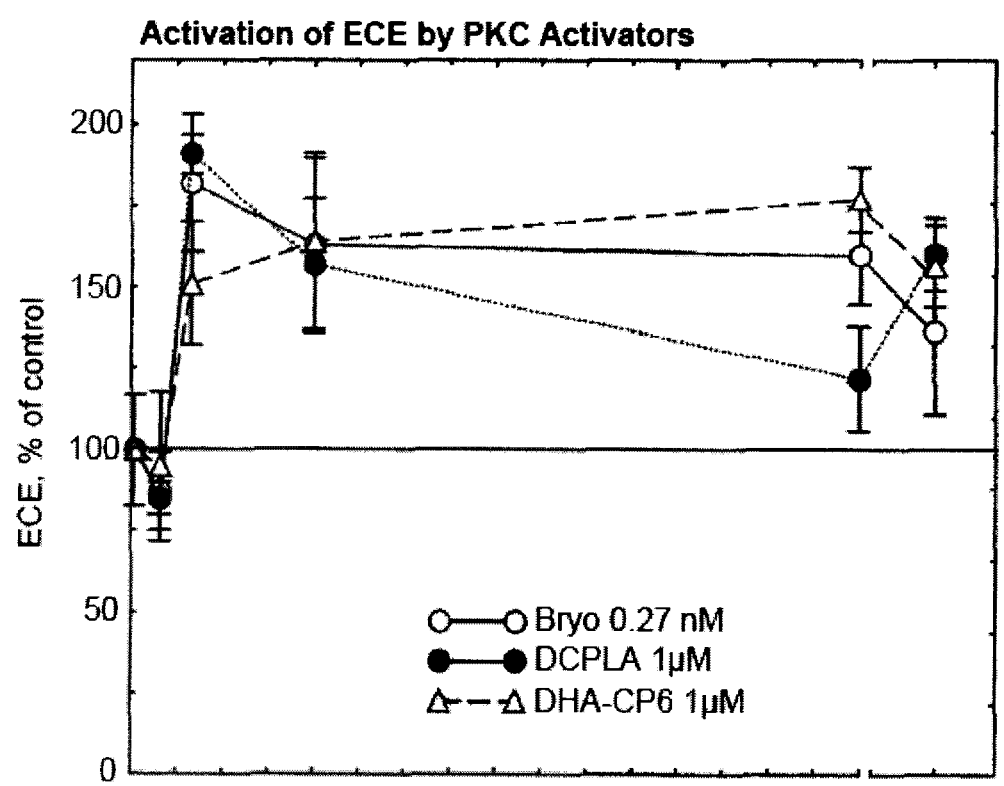
FIG. 12 shows the effect of BR-111 (DHA-CP6) (0.1 μM to 10 μM) on degradation of exogenously applied Aβ in SH-SY5Y neuroblastoma cells.

To determine whether the reduced levels of Aβ caused by PKC activators were due to inhibition of Aβ synthesis or activation of Aβ degradation, BR-111 (DHA-CP6) (0.01 µM to 10 µM) and low concentrations (100 nM) of exogenous monomeric Aβ-42 were applied to cultured SH-SY5Y cells. This concentration of Aβ is too low to produce measurable toxicity or cell death. Since SH-SY5Y cells produce only trace amounts of Aβ, this experiment was an effective test of the ability of PKC activators to enhance Aβ degradation. By 24 hours, most of the Aβ had been taken up by the cells and the concentration of Aβ in the culture medium was undetectable. Addition of 0.01 µM to 10 µM DHA-CP6 to the cells reduced the cellular levels of Aβ by 45%-63%, indicating that the PKCε activator increased the rate of degradation of exogenous Aβ (FIG. 12).

Figure 15:
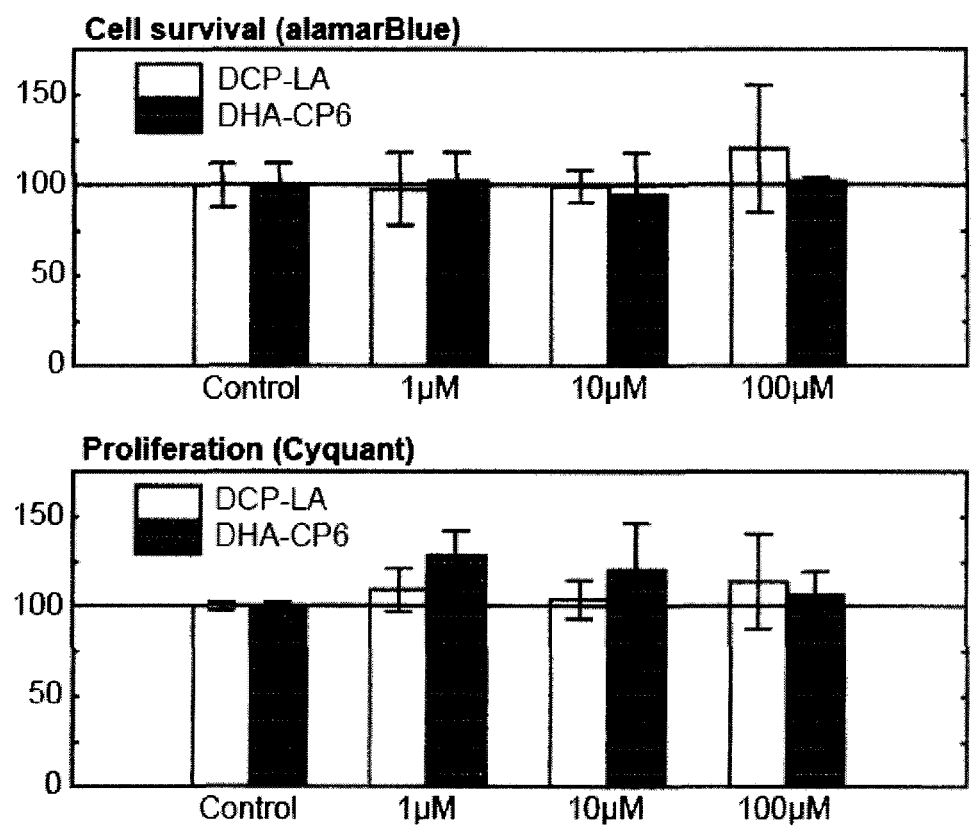
FIG. 15 shows effects of BR-101 (DCP-LA) and BR-111 (DHA-CP6) (1-100 µM) on cell survival and cell proliferation in SH-SY5Y neuroblastoma cells.

DHA-CP6, bryostatin, and DCP-LA had no effect on cell survival or on proliferation as measured by alamar Blue and CyQuant staining (FIG. 15a and FIG. 15b), indicating that the reduction in Aβ production did not result from cell proliferation or a change in cell survival.

Example 8: Effects of PKC Activators on TACE Activity

TACE Assay. TACE was measured by incubating 5 µl cell homogenate, 3 µl buffer (50 mM Tris-HCl 7.4 plus 25 mM NaCl plus 4% glycerol), and 1 µl of 100 µM TACE substrate (Aβz-LAQAVRSSSR-DPa) (Calbiochem) for 20 min at 37° C. 1.5-ml polypropylene centrifuge tubes. Jin et al., *Anal. Biochem.* (2002), vol. 302, pp. 269-275. The reaction was stopped by cooling to 4° C. The samples were diluted to 1 ml and the fluorescence was rapidly measured (ex=320 nm, em=420 nm) in a Spex Fluorolog 2 spectrofluorometer.

Results and Discussion

Figure 13A:
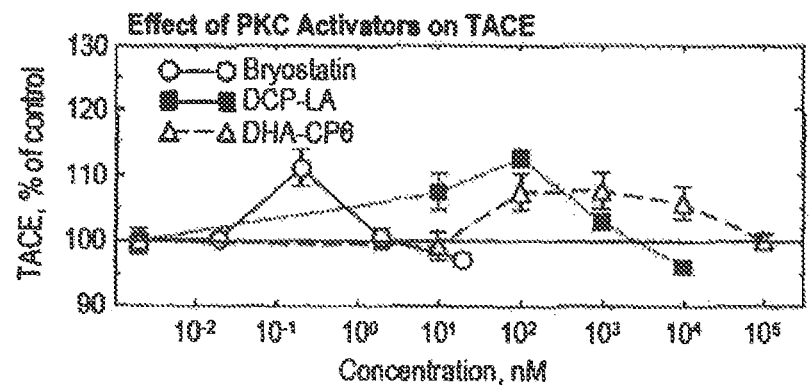
FIGS. 13a, 13b and 13c show effects of (FIG. 13a) bryostatin, BR-101 (DCP-LA) and BR-111 (DHA-CP6) on TACE activity in N2a neuroblastoma cells transfected with human APPSwe/PS1D.
Figure 13B:
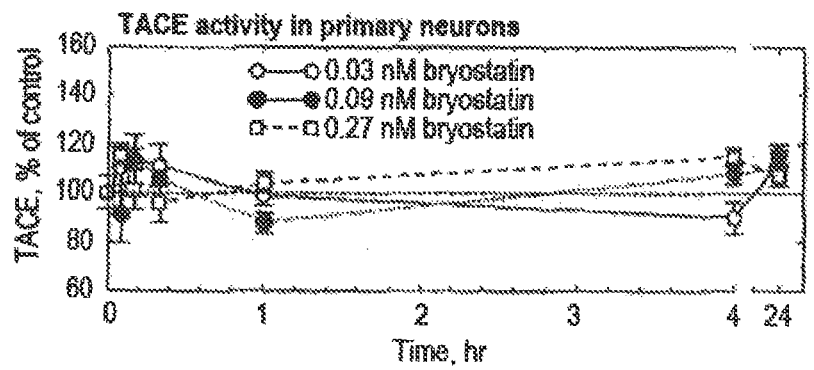
Figure 13C:
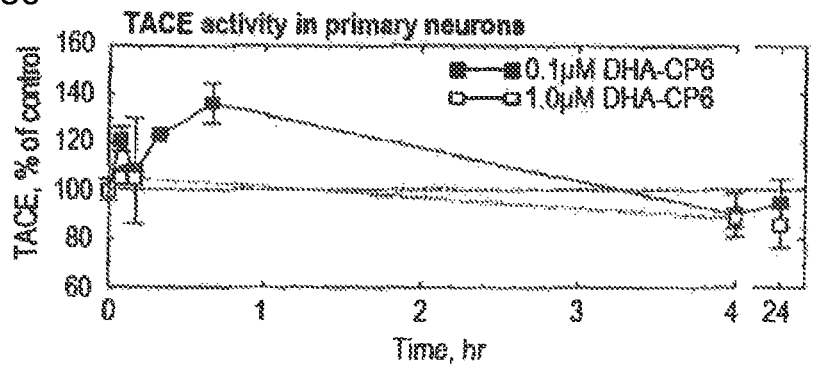

Previous researchers reported that PKC activators such as phorbol 12-myristate 13-acetate produce large increases in TACE activity which correlated with increased sAPPα and decreased Aβ, suggesting that TACE and BACE1 compete for availability of APP substrate, and that PKC activators shift the competition in favor of TACE. Buxbaum et al., *J Biol. Chem.* (1998), vol. 273, pp. 27765-27767; Etcheberrigaray et al., *Proc. Natl. Acad. Sci. USA* (2006), vol. 103, pp. 8215-8220. However, many of these earlier studies were carried out in fibroblasts and other non-neuronal cell types, which appear to respond differently to PKC activators than neurons. For example, Etcheberrigaray et al. found that activation of PKC in human fibroblasts by 10 pM to 100 pM bryostatin increased the initial rate of α-secretase activity by 16-fold and 132-fold, respectively. However, in human SH-SY5Y neuroblastoma cells, N2a mouse neuroblastoma cells (FIG. 13a), and primary neurons from rat hippocampus (FIG. 13b and FIG. 13c), PKC activators bryostatin, BR-101 (DCP-LA) and/or BR-111 (DHA-CP6) only produced small increases in activity. This suggests that any reduction of Aβ levels in neurons by PKC activators must be caused by some other mechanism besides activation of TACE.

Example 9: Effects of PKC Activators on Endothelin-Converting Enzyme (ECE) Activity ECE assay. SH-S757 neuroblastoma cells were incubated with bryostatin (0.27 nM), BR-101 (DCP-LA) (1 µM), and BR-111 (DHA-CP6) (1 µM). Endothelin-converting enzyme (ECE) was measured fluorimetrically using the method of Johnson and Ahn (*Anal. Biochem.* (2000), vol. 286, pp. 112-118). A sample of cell homogenate (20 µl) was incubated in 50 mM MES-KOH, pH 6.0, 0.01% C12E10 (poly-oxyethylene-10-lauryl ether), and 15 µM McaBK2 (7-Methoxycoumarin-4-acetyl [Ala7-(2,4-Dinitrophenyl) Lys9]-bradykinin trifluoroacetate salt) (Sigma-Aldrich).

After 60 min at 37° C., the reaction was quenched by adding trifluoroacetic acid to 0.5%. The sample was diluted to 1.4 ml with water and the fluorescence was measured at ex=334 nm, em=398 nm.

Results and Discussion

Figure 14:
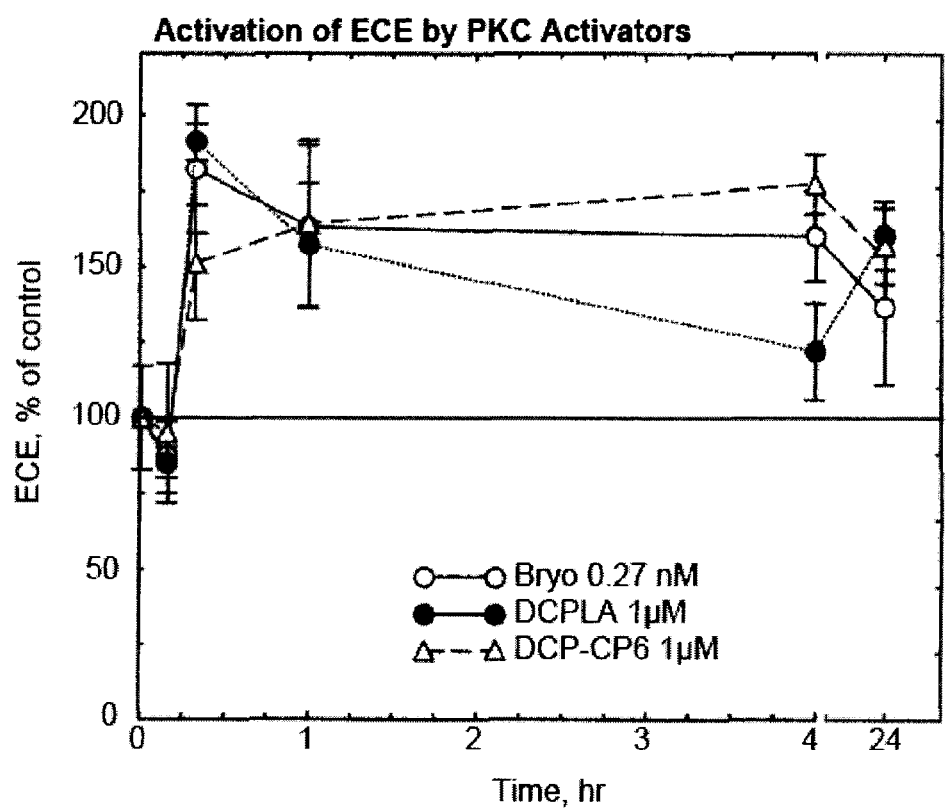
FIG. 14 shows activation of endothelin converting enzyme (ECE) by bryostatin (0.27 nM), BR-101 (DCP-LA) (1 µM), BR-111 (DHA-CP6) (1 µM), and ethanol in SH-SY5Y neuroblastoma cells.

Aβ can be degraded in vivo by a number of enzymes, including insulin degrading enzyme (insulysin), neprilysin, and ECE. PKCε overexpression has been reported to activate ECE. Choi et al., *Proc. Natl. Acad. Sci. USA* (2006), vol. 103, pp. 8215-8220. Thus, the effect of fatty acid derivative PKC activators on ECE was examined. Bryostatin, BR-101 (DCP-LA), and BR-111 (DHA-CP6) all produced a sustained increase in ECE activity (FIG. 14). Since ECE does not possess a diacylglycerol-binding C1 domain, this suggests that the activation by bryostatin was not due to direct activation of ECE, but must have resulted from phosphorylation of ECE or some ECE-activating intermediate by PKC. This result also suggests that indirect activation ECE by PKC activators could be a useful means of reducing the levels of Aβ in patients.

An advantage of compounds that specifically activate PKCε is that they may produce less downregulation than phorbol esters and similar 1,2-diacylglycerol (DAG) analogues. The biphasic response of PKC to DAG-based activators means that a PKC activator may reduce Aβ levels at one time point and increase them at another. Da Cruz e Silva et al., *J. Neurochem.* (2009), vol. 108, pp. 319-330. Careful dosing and monitoring of patients would be required to avoid effects opposite to those intended. The relative inability of compounds to downregulate PKC, such as the fatty acid derivatives disclosed herein, avoids such unintended effects.

Example 10: Global Ischemia Model of Stroke

Rats (male, Wistar, 200-225 g) were randomly divided into 6 groups (8 each) and housed for 1 week before experimentation. Transient or permanent restriction of cerebral blood flow and oxygen supply results in ischemic stroke. The global ischemia model used to induce vascular memory impairment was two-vessel occlusion combined with a short term systemic hypoxia. Ligation of the bilateral common carotid arteries was performed under anesthesia (pentobarbital, 60 mg/kg, i.p.). After a one-week recovery from the surgery, rats were exposed to 14-min hypoxia (5% oxygen in a glass jar). Control rats (sham operated and vehicle controls) were subjected to the same incision to isolate both common carotid arteries and to 14-min air (in the glass jar). Body temperature was kept at 37-37.5° C. using a heating light source during the surgical procedure and until the animals were fully recovered.

Example 11: Bryostatin and MCDA Treatment

Bryostatin-1 was administered at 20) µg/m² (tail i.v., 2 doses/week, for 10 doses), starting 24 hours after the end of the hypoxic event. 4-Methylcatechol-diacetic acid (MCDA, a potential NGF and BDNF booster) was administered at 1.0 mg/kg (i.p., daily for the same 5-week period) in separate groups of rats.

One week after the last bryostatin-1, MCDA, or vehicle administration, rats were. trained in the water maze spatial learning task (2 training trials per day for 4 days), followed by a probe test. A visible platform test was given after the probe test. The results are shown in FIG. 16.

Figure 16:
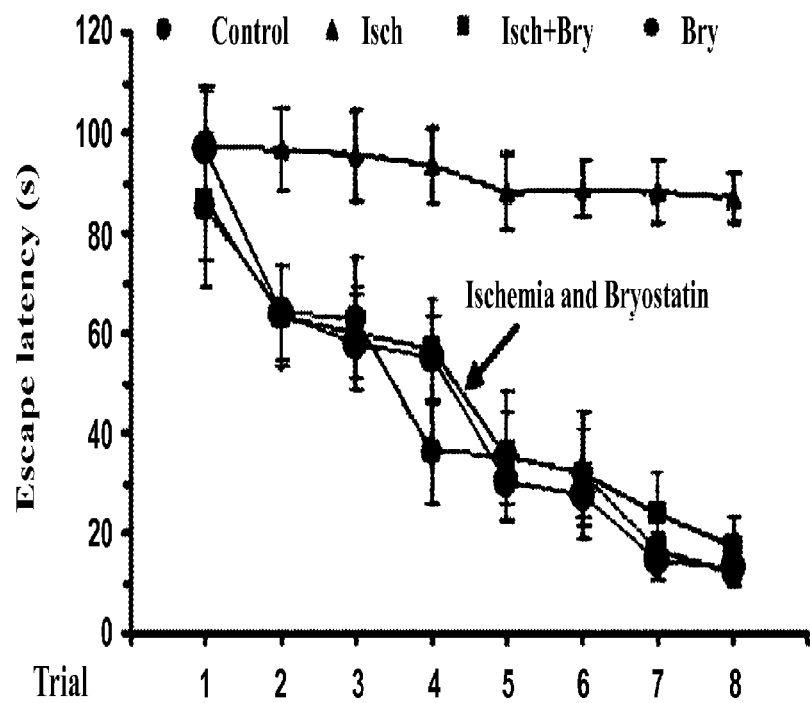
FIG. 16 shows a spatial water maze performance of rats over training trials. Data are shown as means±SEM. Bry, bryostatin-1; Isch, cerebral ischemia; MCDA, 4-methylcatechol-diacetic acid.

Overall, there was a significant learning difference between the 6 groups (FIG. 16; $F_{5,383}$=27.480, p<0.001; ANOVA). Detailed analysis revealed that the ischemic group did not learn the spatial maze task since there was no significant difference in escape latency over trials ($F_{7,63}$=0.102, P>0.05), a significantly impaired learning as compared with the control rats (group difference: $F_{1,127}$=79.751, p<0.001), while the rats in the other 5 groups all learned the task (the ischemic rats with MCDA treatment: p<0.05 and the other 4 groups: p<0.00 lover trials). Bryostatin-1 therapy greatly improved the performance (Ischemic group with bryostatin-1 treatment vs. ischemic rats: $F_{1,127}$=72.782, p<0.001), to the level of performance that did not differ statistically from the control rats (Ischemic group with bryostatin-1 treatment vs. control rats: $F_{1,127}$=0.001, p>0.05). MCDA treatment also improved the learning of the ischemic rats (ischemia with NCDA treatment vs. ischemic rats: $F_{1,127}$=15.584, p<0.001) but the difference between the ischemia with MCDA treatment and control rats remained significant after the 5 week treatment (ischemia with NCDA treatment vs. control rats: $F_{1,127}$=16.618, p<0.001). There were no differences between the control and bryostatin-1-only groups (bryostatin-1 vs. control: $F_{1,127}$=0.010, p>0.05) and between the control and MCDA-only groups (MCDA vs. control: $F_{1,127}$=0.272, p>0.05).

Figure 17:
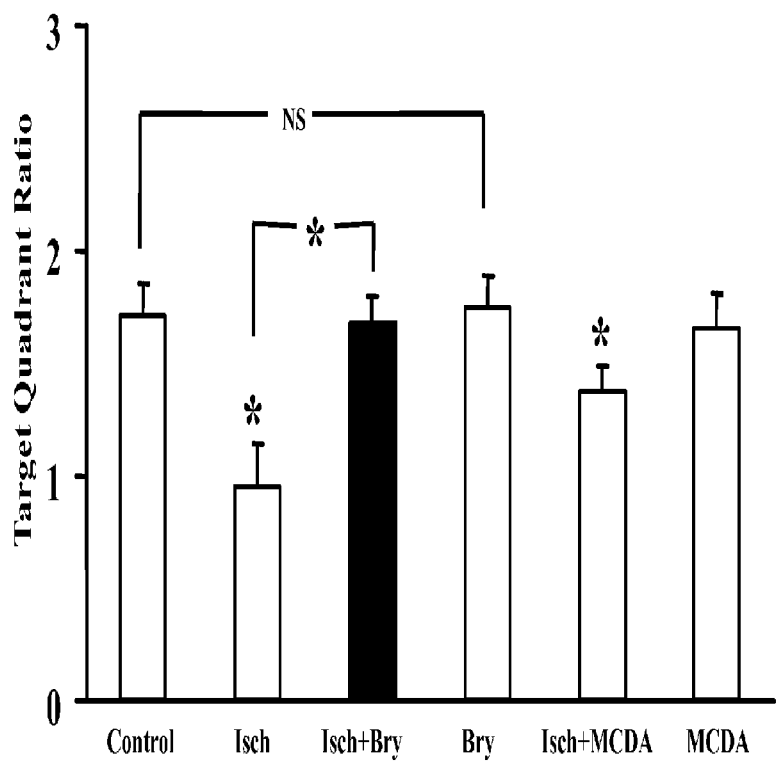
FIG. 17 shows target quadrant ratio during probe test. Bry, bryostatin-1; Isch, ischemia; MCDA, 4-methylcatechol-diacetic acid *: p<0.05. NS: p>0.05.

The rats in the ischemic group did not show a target preference in the probe test (F3,31=0.096, p>0.05), while the rats of the other 5 groups all showed a target quadrant preference in the probe test (all p<0.005). Data were analyzed using target quadrant ratio (dividing the target quadrant distance by the average of the non-target quadrant values during the probe test; FIG. 17). There was a significant difference in the target quadrant ratios between the groups (F5,47=5.081, p<0.001). Detailed analysis revealed group differences between the control and ischemic rats ($F_{1,15}$=9.451, p<0.01), between the ischemic and ischemic with bryostatin-1 treatment ($F_{1,15}$=10.328, p<0.01), and between the ischemic with MCDA treatment and ischemic rats ($F_{1,15}$=5.623, p<0.05), but no differences between the control and ischemic rats with bryostatin-1 treatment ($F_{1,15}$=0.013, p>0.05), between the ischemic with MCDA treatment and control groups ($F_{1,15}$=2.997, p>0.05), between the control and bryostatin-1-only rats ($F_{1,15}$=0.064, p>0.05), and between the control and the MCDA-only rats ($F_{1,15}$=0.0392, p>0.05). A visible platform test, determined after the probe test revealed no significant difference between the groups ($F_{5,47}$=0.115, p>0.05), indicating that there were no significant group differences in sensorimotor ability of the rats.

Example 12: Bryostatin Treatment

Global cerebral ischemialhypoxia was induced in male Wistar rats (225-250 g) by permanently occluding the bilateral common carotid arteries, combined with about 14 minutes of low oxygen (about 5%). Bryostatin-1 was administered at 15 µg/m² (via a tail vein, 2 doses/week, for 10 doses), starting about 24 hours after the end of the ischemic/hypoxic event. Spatial learning (2 trials/day for 4 days) and memory (a probe test of 1 minute, 24 hours after the last trial) task was performed 9 days after the last dose. Overall, there was a significant difference between the groups (F3, 255=31.856, p<0.001) and groups x trials (F21,255=1.648, p<0.05). Global cerebral ischemia impaired the spatial learning (ischemial vs. sham-operated $F_{1,127}$=79.751, p>0.001). The learning impairment was restored by Bryostatin-1 treatment (Bryostatin-1+Ischemia vs. Ischemia:

F1,127=50.233, p<0.001), while Bryostatin-1 alone did not affect the learning (Bryostatin-1 vs. sham-operated: F1,127=2.258, p>0.05; 9 days after the last dose).

In the memory retention test, sham-operated rats showed a target quadrant preference. Such good memory retention was not observed in the ischemic rats, indicating an impaired spatial memory. Bryostatin-1 therapy effectively restored memory retention after ischemia to the level of the sham-operated rats. Bryostatin-1 alone had no significant effects in the target quadrant preference compared with that of the sham-operated control rats. There was a significant difference in the quadrant ratios (calculated by dividing the target quadrant swim distance by the average swim distance in the non-target quadrants; F3,31=6.181, p<0.005) between the groups. Detailed analysis revealed significant differences between the ischemic rats and sham-operated control rats (F1,15=9.451, p<0.001), between the ischemic rats and ischemic rats with Bryostatin-1 treatment (F1,15=10.328, p<0.001), but no significant differences between the ischemic rats with Bryostatin-1 treatment and sham-operated control (F1,15=0.0131, p>0.05) and between the sham-operated control rats and Bryostatin-1 alone rats (F1, 15=0.161, p>0.05). These results demonstrate that the cerebral ischemic/hypoxia produced an impairment of spatial learning and memory, tested about 7 weeks after the ischemic event. The impairment was lasting and not recoverable, during the time frame without appropriate intervention, but restored by chronic Bryostatin-1 treatment, even when the treatment was started 24 hours after the ischemic event, a wide therapeutic time window.

What is claimed:

1. A method of treating a subject who has suffered an ischemic event comprising:
   (a) administering to the subject an anticoagulant and a protein kinase C (PKC) activator within about 24 hours after the ischemic event, wherein the anticoagulant is administered before the PKC activator; and
   (b) administering at least one PKC activator after step (a) for a duration of treatment;
   wherein the PKC activators of step (a) and step (b) are the same or different.

2. The method of claim 1, wherein the anticoagulant is tissue plasminogen activator (TPA).

3. The method of claim 1, wherein the PKC activators of step (a) and step (b) each independently bind to at least one of the 1,2-diacylglycerol (DAG) and 1,2-diacyl-sn-glycero-3-phospho-L-serine (phosphatidyl-L-serine, PS) sites of PKC, or indirectly activate PKC.

4. The method of claim 1, wherein the PKC activators of step (a) and step (b) are each independently chosen from macrocyclic lactones, diacylglycerol derivatives other than phorbol esters, isoprenoids, daphnane-type diterpenes, bicyclic triterpenoids, naphthalenesulfonamides, diacylglycerol kinase inhibitors, growth factor activators, and fatty acids and derivatives thereof.

5. The method of claim 4, wherein the macrocyclic lactones are chosen from bryostatin, bryologs, and neristatin.

6. The method of claim 5, wherein the bryostatin is bryostatin-1.

7. The method of claim 1, wherein in step (a) the anticoagulant is administered within 24 hours after the ischemic event.

8. The method of claim 7, wherein in step (a) the anticoagulant is administered from about 1 hour to about 12 hours after the ischemic event.

9. The method of claim 8, wherein in step (a) the anticoagulant is administered from about 2 hours to about 6 hours after the ischemic event.

10. The method of claim 1, wherein in step (a) the PKC activator is administered within 24 hours after administration of the anticoagulant.

11. The method of claim 10, wherein in step (a) the PKC activator is administered from about 1 hour to about 12 hours after administration of the anticoagulant.

12. The method of claim 11, wherein in step (a) the PKC activator is administered from about 2 hours to about 6 hours after the anticoagulant.

13. The method of claim 1, wherein in step (a) the anticoagulant is administered within about 6 hours after the ischemic event and the PKC activator is administered within about 2 hours after the anticoagulant.

14. The method of claim 13, wherein in step (a) the anticoagulant is administered about 3 hours after the ischemic event and the PKC activator is administered about 2 hours after the anticoagulant.

15. The method of claim 1, wherein the treatment in step (b) is initiated from about 10 hours to about 32 hours after the ischemic event.

16. The method of claim 15, wherein the treatment of step (b) is initiated about 24 hours after the ischemic event.

17. The method of claim 1, wherein in step (b) the PKC activator is administered from 1-3 times per week.

18. The method of claim 1, wherein the duration of treatment in step (b) ranges from about 1 week to about 10 weeks.

19. The method of claim 1, wherein in step (b) the PKC activator is administered by intravenous injection.

20. The method of claim 1, wherein mortality is reduced compared to administration of the anticoagulant alone.

21. The method of claim 20, wherein mortality 24 hours after the stroke is reduced by at least 40%.

22. The method of claim 1, wherein hemorrhagic transformation is reduced compared to administration of the anticoagulant alone.

23. The method of claim 22, wherein the reduction in hemorrhagic transformation is determined by measuring the subject's hemoglobin level compared to administration of the anticoagulant alone.

24. The method of claim 23, wherein the hemoglobin level is reduced by about 50%.

25. The method of claim 1, wherein disruption of the blood-brain barrier is reduced compared to administration of the anticoagulant alone.

26. The method of claim 1, wherein the treatment reverses stroke-induced brain injury.

27. The method of claim 1, wherein the treatment reverses stroke-induced memory impairment.

* * * * *